(12) United States Patent
Tucker et al.

(10) Patent No.: US 7,282,470 B2
(45) Date of Patent: *Oct. 16, 2007

(54) DECONTAMINATION FORMULATION WITH SORBENT ADDITIVE

(75) Inventors: Mark D. Tucker, Albuquerque, NM (US); Robert H. Comstock, Gardendale, AL (US)

(73) Assignee: Sandia Corporation, Albuquerque, NM (US)

( * ) Notice: Subject to any disclaimer, the term of this patent is extended or adjusted under 35 U.S.C. 154(b) by 60 days.

This patent is subject to a terminal disclaimer.

(21) Appl. No.: 10/623,370

(22) Filed: Jul. 18, 2003

(65) Prior Publication Data

US 2004/0022867 A1    Feb. 5, 2004

Related U.S. Application Data

(63) Continuation-in-part of application No. 10/251,569, filed on Sep. 20, 2002.

(60) Provisional application No. 60/397,424, filed on Jul. 19, 2002.

(51) Int. Cl.
| | |
|---|---|
| *A62D 3/00* | (2006.01) |
| *B01F 17/18* | (2006.01) |
| *B01F 17/38* | (2006.01) |
| *C11D 1/62* | (2006.01) |
| *C11D 3/39* | (2006.01) |

(52) U.S. Cl. .................. 510/110; 510/372; 510/504; 588/315; 588/320; 588/400; 588/401; 588/406; 588/408; 588/409; 588/901; 252/186.38; 252/186.41; 252/186.42; 252/186.39

(58) Field of Classification Search ................ 588/200, 588/218, 901; 252/186.38, 186.39, 186.41; 510/110, 370, 372, 504; 516/15
See application file for complete search history.

(56) References Cited

U.S. PATENT DOCUMENTS 3,784,568 A * 1/1974 Kleemann et al. .......... 560/240

(Continued)

FOREIGN PATENT DOCUMENTS

JP    62155203    10/1987

(Continued)

OTHER PUBLICATIONS

James, A.P., et al., "Chemistry of Peroxygen Bleaching," *Chemistry & Industry*, pp. 641-645 (Oct. 15, 1990).

(Continued)

*Primary Examiner*—Joseph D. Anthony
(74) *Attorney, Agent, or Firm*—Robert D. Watson

(57) ABSTRACT

A decontamination formulation and method of making that neutralizes the adverse health effects of both chemical and biological compounds, especially chemical warfare (CW) and biological warfare (BW) agents, and toxic industrial chemicals. The formulation provides solubilizing compounds that serve to effectively render the chemical and biological compounds, particularly CW and BW compounds, susceptible to attack, and at least one reactive compound that serves to attack (and detoxify or kill) the compound. The formulation includes at least one solubilizing agent, a reactive compound, a bleaching activator, a sorbent additive, and water. The highly adsorbent, water-soluble sorbent additive (e.g., sorbitol or mannitol) is used to "dry out" one or more liquid ingredients, such as the liquid bleaching activator (e.g., propylene glycol diacetate or glycerol diacetate) and convert the activator into a dry, free-flowing powder that has an extended shelf life, and is more convenient to handle and mix in the field.

18 Claims, 4 Drawing Sheets

U.S. PATENT DOCUMENTS

| | | | | |
|---|---|---|---|---|
| 3,852,210 | A | * | 12/1974 | Krezanoski ................. 510/372 |
| 3,901,819 | A | * | 8/1975 | Nakagawa et al. ...... 252/186.4 |
| 4,536,314 | A | * | 8/1985 | Hardy et al. ................. 510/376 |
| 4,756,845 | A | | 7/1988 | Sugawara ................... 252/102 |
| 4,850,729 | A | | 7/1989 | Kramer ....................... 401/183 |
| 4,853,143 | A | * | 8/1989 | Hardy et al. ................ 510/312 |
| 4,868,217 | A | | 9/1989 | Araki .......................... 514/642 |
| 5,695,775 | A | * | 12/1997 | von Blucher et al. ....... 424/405 |
| 5,760,089 | A | | 6/1998 | Cronce ....................... 514/643 |
| 6,225,274 | B1 | | 5/2001 | Nitsch ......................... 510/314 |
| 6,245,957 | B1 | | 6/2001 | Wagner ....................... 588/200 |
| 6,448,062 | B1 | * | 9/2002 | Huth et al. .................. 435/264 |
| 6,525,237 | B1 | * | 2/2003 | Purdon et al. .............. 588/317 |
| 6,566,574 | B1 | | 5/2003 | Tadros ......................... 588/200 |
| 6,569,353 | B1 | | 5/2003 | Giletto .................. 252/186.28 |
| 6,723,890 | B2 | * | 4/2004 | Tucker et al. ............... 588/318 |
| 6,827,766 | B2 | * | 12/2004 | Carnes et al. ............ 106/15.05 |

FOREIGN PATENT DOCUMENTS

WO     WO 02/02192 A1 * 1/2002

OTHER PUBLICATIONS

Hoffmann, J., et al., "Bleaching Activators as Acylating Agents: Kinetics of the Acetylation of Piperidine by Some Bleaching Activators", *Journal f. prakt. Chemie.* vol. 332, No. 2, pp. 176-180 (1990).

Wagner, G.W., et al., "Baking Soda, Hydrogen Peroxide, Alcohol, The Refreshing, Universal Decon for VX, GB and HD," *Proc. 1998 ERDEC Scientific Conference on Chemical and Biological Defense Research,* pp. 285-291 (Nov. 18-21, 1997).

* cited by examiner

DECONTAMINATION FORMULATION WITH SORBENT ADDITIVE

CROSS-REFERENCE TO RELATED APPLICATIONS

This application is a continuation-in-part application of U.S. patent application Ser. No. 10/251,569, entitled "Enhanced Formulations for Neutralization of Chemical, Biological and Industrial Toxants", filed on Sep. 20, 2002, now pending and the specification thereof is incorporated herein by reference.

This application claims the benefit of U.S. Provisional Patent Application Ser. No. 60/397,424 entitled "Powdered Additive for DF-200", filed on Jul. 19, 2002, and the specification thereof is incorporated herein by reference.

GOVERNMENT RIGHTS

The Government has rights to this invention pursuant to Contract No. DE-AC04-94AL85000 awarded by the U.S. Department of Energy.

NAMES OF PARTIES TO JOINT RESEARCH AGREEMENT

The names of the parties to the joint research agreement are Sandia Corporation, Albuquerque, N. Mex. and Enviro-Foam Technologies of Huntsville, Ala.

BACKGROUND OF THE INVENTION

The present invention relates to formulations for neutralization of chemical, biological and industrial toxants, and methods of making same.

The present invention is directed to materials and methods for neutralization of toxic chemical, biological and industrial compounds or agents, especially chemical and biological weapons agents, and methods of making same. In particular, the present invention is directed to materials containing solubilizing compounds, reactive compounds, and bleaching activators in powdered form that can be delivered as foams, sprays, liquids, fogs and aerosols to enhance the rate of reactions leading to neutralization of chemical compounds, and other additives which serve to kill or attenuate certain biological compounds or agents. Terrorist threats, potentially involving weapons of mass destruction, are increasing both in the United States and abroad. The use, and threat of use, of chemical and biological agents in the context of weapons of mass destruction are of paramount concern both to national defense as well as to state and local law enforcement.

Certain chemical warfare ("CW") agents known to pose a threat by terrorists share chemical characteristics that present an opportunity for the development of countermeasures. The chemical agents sarin, soman, and tabun (G-agents) are all examples of phosphorus containing compounds which, when altered chemically, can lose their toxicity. Mustard, which is an example of the H-agents, and VX, which is an example of the V-agents, can also be altered chemically and rendered harmless. In addition, certain of the known BW agents include botulinum toxin, anthrax and other spore-forming bacteria, vegetative bacteria, including plague and various viruses can also be deactivated chemically.

A CW or biological warfare ("BW") attack can involve either local placement or wide dispersal of the agent or agents so as to affect a population of human individuals. Because of the flexibility with which CW and BW ("CBW") agents can be deployed, respondents might encounter the agents in a variety of physical states including bulk, aerosol and vapors.

An effective, rapid, and safe (non-toxic and non-corrosive) decontamination technology is required for the restoration of civilian facilities in the event of a domestic terrorist attack. Ideally, this technology should be applicable to a variety of scenarios such as the decontamination of open, semi-enclosed, and enclosed facilities as well as sensitive equipment. Examples of types of facilities where the decontamination formulation may be utilized include a stadium (open), an underground subway station (semi-enclosed), and an airport terminal or office building (enclosed). A foaming version is useful for extending the contact time of the formulation on vertical surface.

Decontamination of chemical compounds has focused primarily on chemical warfare agents, particularly on the nerve agents (such as G agents and V agents) and on the blistering agents (such as mustard gas, or simply, mustard). Reactions involved in detoxification of chemical agents can be divided into substitution and oxidation reactions. Decontamination of biological agents is primarily focused on bacterial spores (e.g., anthrax), which are considered to be the most difficult of all microorganisms to kill. Additional background is discussed in U.S. Pat. No. 6,566,574, "Formulations for Neutralization of Chemical and Biological Toxants", by M. E. Tadros and M. D. Tucker, which is incorporated herein by reference. A need also exists for rapid, safe, and effective neutralization of toxic industrial chemicals, such as Malathion, Hydrogen Cyanide, Sodium Cyanide, Butyl Isocyanate, Carbon Disulfide, and Phosgene gas.

U.S. Pat. No. 6,566,574 is related generally to an aqueous-based decontamination technology ("DF-100") that rapidly neutralizes chemical and biological warfare ("CBW") agents. The formulation:

is effective for neutralizing both chemical and biological agents;
is environmentally benign (i.e., non-toxic and non-corrosive);
works on a number of anticipated material surfaces; and
can be incorporated into a wide variety of carriers (e.g., foams, liquid sprays, fogs) that satisfy a wide variety of operational objectives.

A major interest for the use of the technology was from the civilian first responder (e.g., fire departments, police departments, and HazMat units who would be the first to arrive at the scene of an attack utilizing CBW agents) followed by a secondary interest in use of the formulation for facility restoration. Technical issues exist with DF-100 that make use of the formulation by the civilian first responder less than optimal. These technical problems include: (1) The pH of the DF-100 must be adjusted to optimally decontaminate each specific chemical and biological agent. In other words, a different formulation may be required to neutralize each specific agent. Although it is relatively simple to adjust the pH of the formulation in the laboratory, this is more difficult in the field and is generally unsuitable for the primary users of the technology (i.e., the civilian first responder). (2) The reaction rate for one chemical agent, Mustard, is rather slow as compared to the reaction rates for other chemical agents. These technical problems limit the effectiveness of DF-100 in actual use. A modified formulation, DF-100A, disclosed in U.S. patent application Ser. No. 09/952,940, addressed the requirement to adjust the pH for each specific agent (i.e., the first technical problem described above). However, while DF-100A does improve upon the performance of the formulation at a single pH, it does not completely solve this problem, and does not even address the second technical problem (i.e., the relatively slow reaction rate with Mustard). Additionally, some versions of DF-100/100A can use short-chain alcohols (e.g., isobutanol, isopropanol), which can cause flammability problems if the formulation is packaged in a concentrated form. Also, some versions of DF-100/100A can use diethylene glycol monobutyl ether (DEGMBE), which can cause false alarms on some chemical agent sensors and detectors (especially older sensors that are used in some military settings). As a point of comparison, the following is an example of a preferred formulation for DF-100:

DF-100

2.6% Variquat 80MC (cationic surfactant)
3.3% Adogen 477 (cationic hydrotrope)
0.8% 1-Dodecanol (fatty alcohol)
0.5% Isobutanol (short chain alcohol)
1.6% Isopropanol (short chain alcohol)
0.1% Jaguar 8000 (cationic polymer)
1.6% Diethylene Glycol Monobutyl Ether (solvent)
4% Sodium Bicarbonate (buffer and peroxide activator)
4% Hydrogen Peroxide (liquid oxidant)
75% Water This formulation can be adjusted to a pH value of 8 for optimal decontamination of Mustard and Anthrax spores; and can be adjusted to a pH value of 10.5 for optimal decontamination of VX. Decontamination of chemical agents is generally effective anywhere between pH 8 and 10.

As a further point of comparison, the following is an example of a preferred formulation for DF-100A:

DF-100A 5.3% Variquat 80MC (cationic surfactant)
2.8% Adogen 477 (cationic hydrotrope)
0.65% 1-Dodecanol (fatty alcohol)
0.6% Isobutanol (short chain alcohol)
0.1% Jaguar 8000 (cationic polymer)
1.35% Diethylene Glycol Monobutyl Ether (solvent)
4% Potassium Bicarbonate (buffer and peroxide activator)
4% Hydrogen Peroxide (oxidant)
81% Water This formulation can be adjusted to a pH value of 8 for optimal decontamination of Mustard and Anthrax spores; and can be to a pH value of 10 for optimal decontamination of VX. Decontamination of chemical agents is generally effective anywhere between pH 8 and 10. Also, it can be adjusted to a pH of 9.2 for less than optimal decontamination of all agents.

In both of the examples shown above for DF-100 and DF-100A, the hydrogen peroxide and bicarbonate salt react to produce a highly reactive negatively charged nucleophilic species, hydroperoxycarbonate ($HCO_4^-$), which is a strong oxidant. Other negatively charged nucleophiles are formed by the use of hydrogen peroxide, including: hydroxyl ions ($OH^-$) and hydroperoxide ions ($OOH^-$). The function of the other components in these formulations is discussed extensively in U.S. patent application Ser. Nos. 09/607,586 and 09/952,940.

In U.S. patent application Ser. No. 10/251,569, "Enhanced Formulations for Neutralization of Chemical, Biological and Industrial Toxants", by Tucker and Betty, enhanced decontamination formulations (designated "DF-200") are disclosed that include one or more bleaching activators. The use of a bleaching activator (e.g., peroxide activator or "booster") leads to faster reaction kinetics, improved performance, and the elimination of the need for pH adjustment. Although bleaching activators are commonly used in (anionic) laundry detergents, DF-200 formulations can employ them with cationic surfactants, and where good solubility in water of the activator is useful for achieving quick reaction times.

A desirable bleaching activator for use in DF-200 formulations is preferably water-soluble, non-toxic, non-flammable, and low-cost. The bleaching activator is typically a liquid (e.g., propylene glycol diacetate and glycerol diacetate are liquids at room temperature). Insoluble activators such as TAED can be used, but reaction speeds are limited by how much surface area they have and how quickly they can react with peroxide at the surface. They also leave a sludge that must be dealt with. TAED is used as a perborate activator in laundry products. The above described deficiencies are reduced by following European washing habits, namely using very hot water and front-loading washing machines. TAED cannot be used under USA laundry washing conditions. Further, for decontamination systems, a sludge of insoluble material left in the tank of a spray application decontamination device would build up and eventually plug the pump or nozzle, and/or cause other problems. However, if the bleaching activator component of a kit configuration for DF-200 could be provided in a more convenient, soluble, non-liquid form, such as the dry, free-flowing powder described herein, then handling and mixing of the beaching activator with the other kit components of the decontamination formation would be easier and more convenient, especially when making up the formulation in the field. Additionally, such a dry powder material could be packaged along with a desiccant for superior moisture protection and would have an extended shelf life, be fast reacting, and would leave no sludge.

Against this background, the present invention was developed.

SUMMARY OF THE INVENTION

A decontamination formulation and method of making that neutralizes the adverse health effects of both chemical and biological compounds, especially chemical warfare (CW) and biological warfare (BW) agents, and toxic industrial chemicals. The formulation provides solubilizing compounds that serve to effectively render the chemical and biological compounds, particularly CW and BW compounds, susceptible to attack, and at least one reactive compound that serves to attack (and detoxify or kill) the compound. The formulation includes at least one solubilizing agent, a reactive compound, a bleaching activator, a sorbent additive, and water. The highly adsorbent, water-soluble sorbent additive (e.g., sorbitol or mannitol) is used to "dry out" one or more liquid ingredients, such as the liquid bleaching activator (e.g., propylene glycol diacetate or glycerol diacetate) and convert the activator into a dry, free-flowing powder that has an extended shelf life, and is more convenient to handle and mix in the field.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
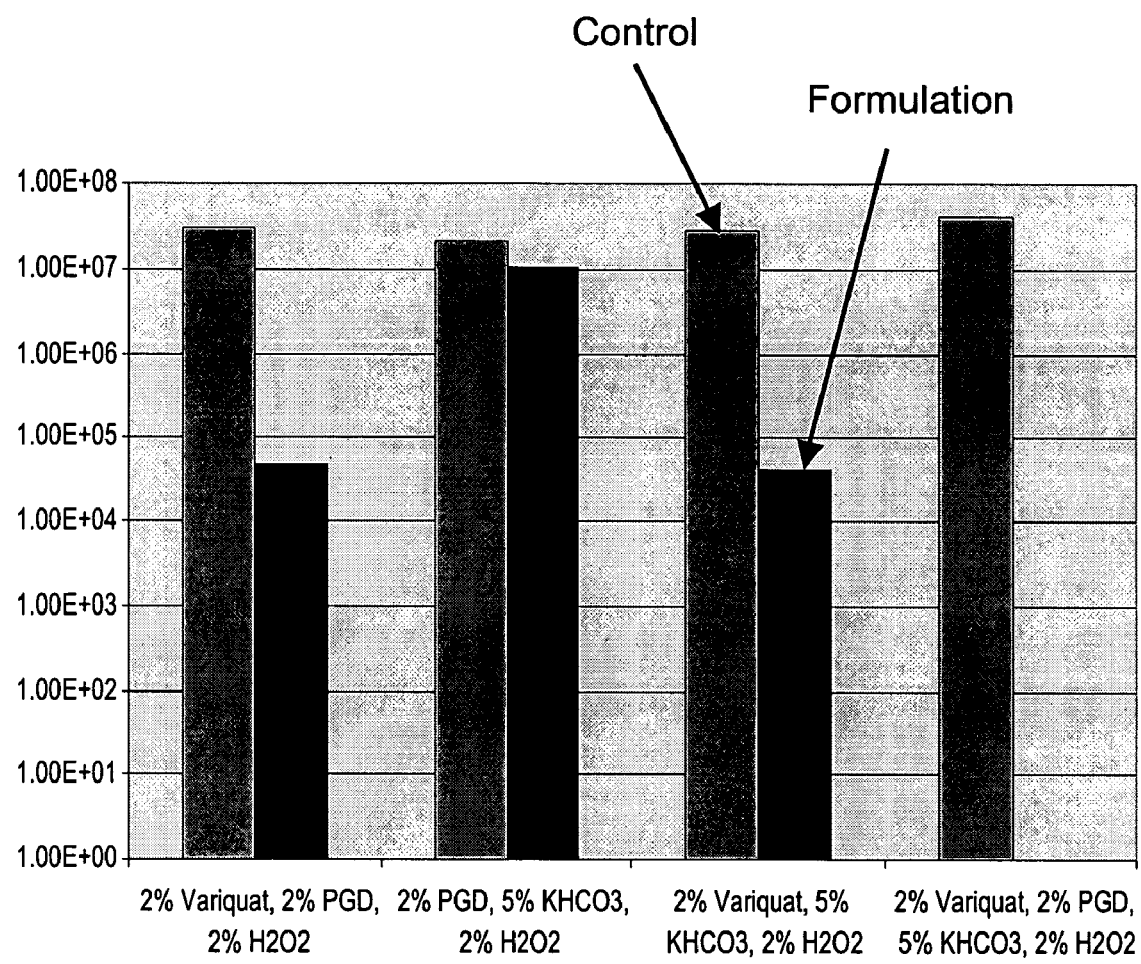
FIG. 1 is a graph of the effect of various combinations of DF-200 components on *Bacillus globigii* (anthrax simulant) spore kill.

The present invention addresses the need for a general formulation that neutralizes the adverse effects of either or both chemical and biological toxants, where a toxant is defined as any chemical or biological compound, constituent, species, or agent that through its chemical or biological action on life processes can, if left untreated, cause death, temporary incapacitation, or permanent harm to humans or animals. This includes all such chemicals or biological agents, regardless of their origin or of their method of production, and regardless of whether they are produced in facilities, in munitions or elsewhere. Neutralization is defined as the mitigation, de-toxification, decontamination, or otherwise destruction of toxants to the extent that the toxants no longer cause acute adverse effects to humans or animals. The formulation and described variations of the present invention can neutralize, and does not itself contain or produce, infection, significant adverse health effects, or even fatality in animals.

An important subset of chemical and biological compounds that the present invention addresses is that of chemical warfare ("CW") and biological warfare ("BW") agents. However, the present invention also addresses toxants that can cause potential adverse health effects to animals, including humans, where such adverse health effects include infections, acute and chronic health effects, and fatalities. Such toxants can be found in an agricultural facility, animal or dairy farm, or food products processing or packaging facility. Additionally, the present invention addresses the need for such a formulation that is itself non-toxic and non-corrosive, and that can be delivered by a variety of means and in different phases.

The word "formulation" is defined herein as the activated product or solution (e.g., aqueous solution) that is applied to a surface or body for the purpose of neutralization, with or without the addition of a gas (e.g., air) to create foam. Unless otherwise specifically stated, the concentrations, constituents, or components listed herein are relative to the weight percentage of the overall activated solution. The word "water" is defined herein to broadly include: pure water, tap water, deionized water, demineralized water, saltwater, or any other liquid consisting primarily of $H_2O$.

One example of a minimum set of constituents for a DF-200 formulation that can achieve a significant rate of spore kill comprises four components:

(1) a solubilizing agent selected from the group consisting of a cationic surfactant (e.g., Variquat 80MC), a cationic hydrotrope (e.g., Adogen 477), and a fatty alcohol (e.g., 1-Dodeconal);

(2) a beaching activator selected from the group consisting of O-acetyl, N-acetyl, and nitrile group peroxide activators (e.g., propylene glycol diacetate);

(3) a reactive compound (e.g., hydrogen peroxide, peracetic acid); and (4) water.

The solubilizing agent serves to effectively render the toxant susceptible to attack, while the reactive compound serves to attack and neutralize the toxant, and the bleaching activator enhances the process.

Examples of suitable cationic surfactants include: quaternary ammonium salts and polymeric quaternary salts. Examples of suitable quaternary ammonium salts include: cetyltrimethyl ammonium bromide, benzalkonium chloride, benzethonium chloride, cetylpyridinium chloride, alkyldimethylbenzylammonium salt, and tetrabutyl ammonium bromide. A preferred cationic surfactant is VARIQUAT 80MC™ (which used to be supplied by WITCO, Inc., but now is supplied by Degussa Goldschmidt), which is a mixture of benzyl (C12-C16) alkyldimethylammonium chlorides. The concentration of quaternary ammonium salt used in DF-200 formulations is preferably no more than about 10%, because at higher concentrations the quaternary ammonium salt becomes significantly toxic to humans and the environment.

Examples of suitable cationic hydrotropes include: tetrapentyl ammonium bromide, triacetyl methyl ammonium bromide, and tetrabutyl ammonium bromide. A preferred cationic hydrotrope is ADOGEN 477™ (which used to be supplied by WITCO, Inc., but now is supplied by Degussa Goldschmidt), which is a pentamethyltallow alkyltrimethylenediammonium dichloride.

Examples of suitable fatty alcohols include alcohols having 8-20 carbon atoms per molecule, such as: 1-dodecanol, pure dodecanol, hexadecanol, and 1-tetradecanol.

Examples of suitable bleaching activators are discussed subsequently.

Examples of suitable reactive compounds include: peroxide compounds; hydrogen peroxide; urea hydrogen peroxide; sodium perborate; sodium percarbonate; sodium carbonate perhydrate; sodium peroxypyrophosphate; sodium peroxysilicatehydrogen; peroxide adducts of pyrophosphates; citrates; sodium sulfate; urea; and sodium silicate; an activated peroxide compound (e.g., hydrogen peroxide+bicarbonate); peracetic acid; oximates (e.g., butane-2,3-dione, monoooximate ion, and benzohydroxamate); alkoxides (e.g., methoxide and ethoxide); aryloxides (e.g., aryl substituted benzenesulfonates); aldehydes (e.g., glutaraldehyde); peroxymonosulfate; Fenton's reagent (a mixture of iron and peroxide); and sodium hypochlorite. Use of these reactive compounds in DF-200 formulations can produce a variety of negatively-charged nucleophiles, e.g., hydroxyl ions ($OH^-$) and hydroperoxide ions (($OOH^-$) produced when using hydrogen peroxide; and/or hydroperoxycarbonate ions ($HCO_4^-$) produced when hydrogen peroxide is combined with a carbonate salt. Hydroperoxycarbonate ions ($HCO_4^-$) are a much stronger oxidant than hydroxyl ions ($OH^-$) or hydroperoxide ions (($OOH^-$), and are especially effective in reacting with biological toxants. When using hydrogen peroxide in DF-200 formulations, its concentration is preferably less than about 10% because higher concentrations are significantly corrosive, especially in the range of 30-50% hydrogen peroxide concentration.

To achieve very high rates of spore kill, a carbonate salt (e.g., sodium bicarbonate or potassium bicarbonate) is preferably added to the minimum set of constituents for DF-200 formulations described above. When using a peroxide compound (e.g., hydrogen peroxide) as the reactive compound for DF-200, the added carbonate salt combines with, e.g., hydrogen peroxide to form the highly reactive hydroperoxycarbonate species ($HCO_4^-$). Addition of carbonate salts can also buffer the formulation to optimize the pH.

Hence, a minimum set of constituents for DF-200 formulations that can achieve a very high rate of spore kill can comprise five components:

(1) a solubilizing agent selected from the group consisting of a cationic surfactant (e.g., Variquat 80MC), a cationic hydrotrope (e.g., Adogen 477), and a fatty alcohol (e.g., 1-Dodeconal);

(2) a beaching activator selected from the group consisting of O-acetyl, N-acetyl, and nitrile group peroxide activators (e.g., propylene glycol diacetate);

(3) a reactive component (e.g., hydrogen peroxide, peracetic acid, etc.);

(4) a carbonate salt (e.g., sodium bicarbonate); and (5) water.

Examples of suitable carbonate salts include: potassium bicarbonate, sodium bicarbonate, ammonium bicarbonate, ammonium hydrogen bicarbonate, lithium bicarbonate, ammonium carbonate, and potassium carbonate.

FIG. 1 shows the results of decontamination tests on *Bacillus globigii* spores (initial concentration $10^7$ spores/ml). The spores were exposed to four different sub-combinations of the various components of DF-200 formulations for 1 hour (the pH of the formulation was 9.8). The degree of spore kill was determined by culturing surviving organisms. As shown in FIG. 3, significant spore kill was achieved by using two different combinations: (1) an aqueous solution of 2% Variquat (cationic surfactant), 2% propylene glycol diacetate (bleaching activator), and 2% hydrogen peroxide (oxidant) and (2) an aqueous solution of 2% Variquat (a cationic surfactant), 5% potassium bicarbonate (buffer and peroxide activator) and 2% hydrogen peroxide (oxidant). However, very high spore kill was achieved by using a third combination, comprising (3) an aqueous solution of 2% Variquat (a cationic surfactant), 2% propylene glycol diacetate (bleaching activator), 5% potassium bicarbonate (buffer and peroxide activator) and 2% hydrogen peroxide (oxidant).

Next, a variety of alternative embodiments and configurations of DF-200 formulations will be presented.

DF-200HF (High Foam)

An example of a "high-foaming" formulation for DF-200HF comprises:

DF-200HF (High Foam)

1-4% (preferably 2%) Variquat 80MC (cationic surfactant)

0.5-3% (preferably 1%) Adogen 477 (cationic hydrotrope)

0.2-0.8% (preferably 0.4%) 1-Dodecanol (fatty alcohol)

0.05-0.1% Jaguar 8000 (cationic water-soluble polymer)

0.5% Di(propylene glycol) Methyl Ether (solvent)

0.1-10% (preferably 1-4%) Hydrogen Peroxide (oxidant)

0.1-10% (preferably 2-8%) Bicarbonate salt (buffer and peroxide activator)

1-4% Propylene Glycol Diacetate or Glycerol Diacetate (bleaching activator)

67-97% Water

This formulation is effective at a pH value between 7.5 and 10.5. This formulation can be adjusted to a pH value between 9.6 and 9.8 for optimal decontamination of all target agents. This "high-foam" formulation includes a cationic water-soluble polymer (e.g., Jaguar 8000™ or), which increases the bulk viscosity of the solution and produces a more stable foam. Some examples of other suitable non-anionic water-soluble polymers include: polyvinyl alcohol, guar gum, (cationic or non-ionic) polydiallyl dimethyl ammonium chloride, polyacrylamide, polyethylene glycol 8000 (e.g., PEG 8000), and Jaguar 8000™ (Guar Gum 2-hydroxypropyl ether). A cationic polymer is preferred over a non-ionic polymer; an anionic polymer does not work well. The fatty alcohol 1-dodecanol serves to increase the surface viscosity of the foam lamellae to also increase foam stability against drainage and bubble collapse. Other foaming agents may also be included in the high-foaming formulations, namely Celquat SD 240c (at about 0.15%) and/or Lumulse POE 12 (at about 4%).

DF-200LF (Low Foam)

An example of a "low-foaming" formulation for DF-200LF comprises:

DF-200LF (Low Foam)

4% Variquat 80MC (cationic surfactant)

0.4% Lauramide DEA [N,N-Bis(2-Hydroxyethyl)-Dodecanamide] (foam booster)

1-4% Propylene Glycol Diacetate or Glycerol Diacetate (bleaching activator)

0.5% Di(propylene glycol) Methyl Ether (solvent)

0.05-0.1% Jaguar 8000 Polymer (cationic water-soluble polymer)

0.1-10% (preferably 1-4%) Hydrogen Peroxide (oxidant)

0.1-10% (preferably 2-8%) Bicarbonate salt (buffer and peroxide activator)

71-94% Water

This formulation is generally effective at a pH value between 7.5 and 10.5. This formulation can be adjusted to a pH value between about 9.6 and 9.8 for optimal decontamination of all target agents.

The term 'High Foam' refers to the ability of a formulation to form a highly stable and persistent foam, whereas a 'Low Foam' formulation forms a much less stable foam. The following tables show the improved performance of DF-200HF and DF-200LF as compared to DF-100A. The notation "ND" refers to a concentration below detectable limits, and "PGDA" refers to propylene glycol diacetate (a preferred bleaching activator).

TABLE 1

Summary of the reaction rates for Mustard simulant (2-Chloroethyl phenyl sulfide).

| | Mustard Simulant (% Decontaminated) | | |
|---|---|---|---|
| Formulation | 1 Minute | 15 Minutes | 60 Minutes |
| DF-100A (pH 8) | 18 | 42 | 81 |
| DF-100A (pH 9.2) | 16 | 38 | 83 |

TABLE 1-continued Summary of the reaction rates for Mustard simulant (2-Chloroethyl phenyl sulfide).

| Formulation | Mustard Simulant (% Decontaminated) | | |
|---|---|---|---|
| | 1 Minute | 15 Minutes | 60 Minutes |
| DF-200HF (2% PGDA/3% H$_2$O$_2$/4.5% Bicarb) | 42 | 62 | ND |
| DF-200HF (2% PGDA/3.5% H$_2$O$_2$/4% Bicarb) | 94 | 98 | ND |
| DF-200LF (2.5% PGDA/3% H$_2$O$_2$, 4.5% Bicarb) | 55 | 91 | ND |

TABLE 2

Summary of the reaction rates for VX simulant (O-Ethyl S-Ethyl Phenylphosphonothioate).

| Formulation | VX Simulant (% Decontaminated) | | |
|---|---|---|---|
| | 1 Minute | 15 Minutes | 60 Minutes |
| DF-100A (pH 10) | 45 | 99 | ND |
| DF-100A (pH 9.2) | 33 | 71 | 93 |
| DF-200HF (2% PGDA/3% H$_2$O$_2$/4.5% Bicarb) | 63 | 98 | ND |
| DF-200HF (2% PGDA/3.5% H$_2$O$_2$/4% Bicarb) | 66 | 99 | ND |
| DF-200LF (2.5% PGDA/3% H$_2$O$_2$/4.5 Bicarb) | 79 | 98 | ND |

TABLE 3

Summary of the reaction rates for G Agent simulant (Diphenyl chlorophosphate).

| Formulated | G Agent Simulant (% Decontaminated) | | |
|---|---|---|---|
| | 1 Minute | 15 Minutes | 60 Minutes |
| DF-100A (pH 8) | 53 | ND | ND |
| DF-100A (pH 9.2) | ND | ND | ND |
| DF-200HF (2% PGDA/3% H$_2$O$_2$/4.5 Bicarb) | ND | ND | ND |
| DF-200HF (2% PGDA/3.5% H$_2$O$_2$ 4% Bicarb) | ND | ND | ND |
| DF-200LF (2.5% PGDA/3% H$_2$O$_2$ 4.5% Bicarb) | ND | ND | ND |

TABLE 4

Summary of the kill rates for Anthrax simulant (*Bacillus globigii* spores)

| Formulation | Anthrax Simulant % Kill after 30 Minutes | Anthrax Simulant % Kill after 60 Minutes |
|---|---|---|
| DF-100A (pH 8) | 99.99 | 99.99999 |
| DF-100A (pH 9.2) | 90 | 99.9 |
| DF-200HF (2% PGDA/3% H$_2$O$_2$/4.5 Bicarb) | 99.99999 | 99.99999 |
| DF-200LF (2.5% PGDA/3% H$_2$O$_2$/4.5 Bicarb) | 99.99999 | 99.99999 |

Differences between formulations of DF-200 and DF-100/100A include:

DF-200 is active against all agents at a single pH. The formulation is effective at pH values between about 7.5 and 10.5; is more effective at pH values between about 9.2 and 9.8; and is most effective at pH values between about pH 9.6 and 9.8;

DF-200 has better performance against Mustard;

DF-200 has better performance against bacterial spores;

DF-200 has lower concentrations of both the cationic surfactant and/or the cationic hydrotrope, which further lowers the (already low) toxicity and corrosivity properties of the formulation;

DF-200 has a lower concentration of the foam stability component, 1-Dodecanol;

DF-200 doesn't use a short-chained alcohol (e.g., isobutanol, isopropanol), which causes flammability problems when the formulation is packaged in a concentrated form;

Some embodiments of DF-200 don't use Diethylene Glycol MonoButyl Ether (DEGMBE), which can cause false alarms on some chemical agent sensors and detectors (especially older sensors which are used in some military settings); and DF-200 can contain a lower concentration of hydrogen peroxide, which also reduces the (already low) toxicity and corrosivity properties of the formulation.

Additional differences between DF-200 and DF-100A include:

DF-200 performs optimally at a higher pH (about 9.6 to 9.8) as compared to DF-100A. However, note that this is the typical pH value for common household products such as laundry detergents, shampoos, and dishwashing detergents; and DF-200 has more individual components that should be stored separately (e.g., the hydrogen peroxide and the bleaching activator) from the bulk formulation until use, as compared to DF-100A (where only one component, hydrogen peroxide, should be stored separately). This will be discussed in greater detail below.

One reason for the better performance of DF-200 formulations (e.g., DF-200HF and DF-200LF) over DF-100 and DF-100A formulations is the addition of a bleaching activator (e.g., propylene glycol diacetate). Bleaching activators can be compounds with O— or N— bounded acetyl groups that react with the strongly nucleophilic hydroperoxy anion (OOH$^-$) to yield peroxygenated species, which are more efficient oxidizers than hydrogen peroxide alone.

$$\underset{RC-L}{\overset{O}{\|}} + OOH^- \longrightarrow \underset{RC-OOH}{\overset{O}{\|}} + L^-$$

Since the 1950's, a number of different bleaching activators have been used in commercial laundry detergents, as well as other commercial products. The most common activators are tetraacetyl ethylenediamine (TAED), which is primarily used in Europe and Asia; and n-nonanoyloxybenzenesulfonate (NOBS), which is primarily used in the United States. NOBS is a proprietary chemical of the Proctor and Gamble company. In a laundry detergent, hydrogen peroxide is provided in a solid form (usually as sodium perborate, which reacts in water to form the hydroperoxy anion). The addition of a bleaching activator greatly enhances the ability of a laundry detergent to remove stains from clothing.

It should be noted that TAED and NOBS bleaching activators are extremely insoluble in water (e.g., TAED is only 0.1% soluble at 25° C.). To get around this problem in a laundry detergent, the solid TAED or NOBS particles are kept in suspension by the agitating action of the washing machine, where they slowly react with the hydrogen peroxide in the detergent. However, agitation in the field of DF-200 formulations presents practical problems; hence, a water-soluble bleaching activator is preferred.

Useful water-soluble bleaching activators include short-chained organic compounds that contain an ester bond, e.g., ethylene glycol diacetate, propylene glycol monomethyl ether acetate, methyl acetate, dimethyl glutarate, diethylene glycol monoethyl ether acetate, glycerol diacetate (Diacetin), glycerol monoacetate, glycerol triacetate, and propylene glycol diacetate. A preferred water-soluble bleaching activator is propylene glycol diacetate (PGDA), which is shown below.

This molecule reacts with hydroperoxy anions (OOH$^-$), giving up the ester bonds to form two peroxygenated molecules.

Propylene glycol diacetate also acts as an organic solvent that is highly effective in solubilizing insoluble organic molecules (e.g., chemical warfare agents, as well as foam stabilizers/boosters (such as 1-dodecanol and Lauramide DEA)). Therefore, an added function of this compound is that it can be used to supplement the diethylene glycol monobutyl ether (DEGMBE) solvent that is used in DF-100 and DF-100A, or to supplement the Di(propylene glycol) methyl ether solvent used in some DF-200 formulations, thereby allowing the propylene glycol diacetate to serve a dual purpose (i.e., solvent and bleaching activator).

Bleaching activators are generally not stable in water for long periods of time. This is especially true when the aqueous solution is at a high pH (>10). Therefore, for long shelf life, the propylene glycol diacetate (or other bleaching activator) is preferably stored separate from the aqueous solution until use. This is not unlike other products that utilize bleach activators (e.g., laundry detergents), where all the components of the formulation are kept dry and separated until use (in the case of laundry detergent, the bleaching activator is encapsulated to prevent it from reacting with the peroxide component until both components are mixed in water).

Another example of a water-soluble bleaching activator is ethylene glycol diacetate, which works well in DF-200 formulations. However, when ethylene glycol diacetate reacts with hydrogen peroxide, it forms ethylene glycol (i.e., anti-freeze), which is a relatively toxic byproduct. Propylene glycol diacetate, on the other hand, does not form this relatively toxic byproduct.

DF-200NF (Non-Foaming)

An example of a non-foaming DF-200 formulation comprises (amounts illustrative):

DF-200NF (Non-Foaming)

1-10% (preferably 2.5%) Benzalkonium Chloride (cationic surfactant)

1-8% Propylene Glycol Diacetate or Glycerol Diacetate (bleaching activator)

1-16% Hydrogen Peroxide (oxidant)

2-8% Potassium Bicarbonate (buffer and peroxide activator)

65.5-93.5% Water

The formulation can be adjusted to a pH value between about 9.6 and 9.8 for optimum performance, and is effective for decontamination of all target agents.

DF-100E

An example of an enhanced version of DF-100A that utilizes the propylene glycol diacetate bleaching activator comprises (amounts illustrative):

DF-100 E 5.3% Variquat 80MC
2.8% Adogen 477
0.65% 1-Dodecanol
0.5% Isobutanol
0.1% Jaguar 8000
1.35% Diethylene Glycol Monobutyl Ether
2-8% Bicarbonate Salt
1-4% Hydrogen Peroxide
1-4% Propylene Glycol Diacetate or Glycerol Diacetate
73-85% Water This formulation can be adjusted to a pH value between about 9.6 and 9.8 for optimal performance against all agents. The performance of DF-100E (2% PGDA/3.00% $H_2O_2$/3.75% Bicarbonate salt) against chemical simulants is shown below in Table 5:

TABLE 5

Summary of the reaction rates for the DF-100E formulation in kinetic testing.

| | % Decontaminated | | |
|---|---|---|---|
| Simulant | 1 Minute | 15 Minutes | 60 Minutes |
| Mustard HD | 83 | 92 | ND |
| G Agents | ND | ND | ND |
| VX | 66 | 96 | ND |

Tests against the anthrax spore simulant (Bacillus globigii spores) demonstrated 99.9999% (7-Log) kill after a 30 minute exposure to DF-100E.

Other bleaching activators (such as water-insoluble NOBS or TAED) can be used in place of Propylene Glycol Diacetate in DF-100E. However, as noted above, this produces a slurry mixture instead of a true liquid solution.

The following table summarizes some differences between DF-100, DF-100A, DF-100E, DF-200HF, DF-200LF, DF-200NF, and DF-200HF Slurry:

TABLE 6

Comparison of Various Decontamination Formulations

| Formulation | Requires pH Adjustment | Improved Kinetics | Reduction of Flammable Constituents | Forms Highly Stable Foam | Can Use Saltwater for Makeup Water |
|---|---|---|---|---|---|
| DF-100 | Y | N | N | Y | N |
| DF-100A | N | N | N | Y | N |
| DF-100E | N | Y | N | Y | Y |
| DF-200HF | N | Y | Y | Y | Y |
| DF-200LF | N | Y | Y | N | Y |

TABLE 6-continued

Comparison of Various Decontamination Formulations

| Formulation | Requires pH Adjustment | Improved Kinetics | Reduction of Flammable Constituents | Forms Highly Stable Foam | Can Use Saltwater for Makeup Water |
|---|---|---|---|---|---|
| DF-200NF | N | Y | Y | N | Y |
| DF-200HF-Slurry | N | Y | Y | Y | Y |

Kit Configurations

In the following sections, various examples of 2-part, 3-part, and 4-part "kit" configurations are shown for the different embodiments of DF-200 formulations. In general, the 2-part and 3-part kits have the bulk of the water already "pre-packaged" in one of the two (or three) containers (usually the foam component). This allows for rapid deployment of the decontamination solution, the use of small-scale units (e.g., backpacks), and doesn't require any extra water to be provided in the field.

Conversely, the 4-part kits generally require that the make-up water is added in the field at, or near, the site of contamination. This allows the "package" containing the other three parts to be much lighter, which makes it easier to ship and store. However, a source of make-up is required in the field (which can be saltwater).

In general, the DF-200 formulations can be configured either way, with the bulk of the water "pre-packaged", or without, depending on the application.

DF-200HF (Kit Configuration)

The DF-200HF formulation can be configured as a 4-part kit, and then prepared for field use as follows (amounts illustrative):

DF-200 HF (4-Part Kit)

Part A (Foam Concentrate):
  20 g Variquat 80MC
  10 g Adogen 477
  4 g b-Dodecanol
  1 g Jaguar 8000 Polymer
  5 g Di(propylene glycol) methyl ether
  7.5 g Potassium Bicarbonate
  141 g Water Part B (Solid Component):
  50 g Sodium Percarbonate
  50 g Urea Hydrogen Peroxide Part C (Bleaching Activator):
  20 g Propylene Glycol Diacetate or Glycerol Diacetate Part D (Make-up Water):
  800 g Water In this example of a 4-part configuration, the bulk of the water is not included in the "package" (i.e., Parts A, B, and C), which minimizes the weight of the package for shipping and storage. Here, the make-up water (Part D) would be supplied in the field at, or near, the site of contamination. The pH of the formulation can be adjusted to be between about 9.6 and 9.8 for optimal performance. The formulation as described above will produce 1 liter of "high" foam solution. In this example, sodium percarbonate supplies a portion of the hydrogen peroxide, a portion of the bicarbonate, and a base for buffering the solution. The remainder of the hydrogen peroxide is supplied by the urea hydrogen peroxide. The total hydrogen peroxide concentration is approximately 3% in this example. The viscosity of the formulation can be adjusted to be between about 4-9 mm$^2$/s.

A variety of different methods can be used in the field to mix the DF-200HF formulation configured as a 4-part kit, for example:

Method 1: Supply the make-up water (Part D). Then, mix Part B into Part D. Then, add Parts C and A to Part B+D. Use, preferably, within 8 hours.

Method 2: Mix Part C into Part A. Supply the make-up water (Part D). Then, mix Part B into Part D. Keep separate until use. When use is required, mix Part A+C into Part B+D. Use, preferably, within 8 hours of first mixing Parts A+C into Parts B+D.

In general, activated DF-200 formulations are used preferably within 8 hours after mixing, however, they still can be effective for up to 24 hours and longer. DF-200HF (High Foam) can be applied to a surface for a long period of time, and then rinsed off. However, DF-200LF (Low Foam) can be used in a different manner than the DF-100/100A and DF-200HF formulations. Instead of leaving DF-200LF on a surface for long periods of time, it can be applied to a surface, left for a relatively short period of time (e.g., 15-60 minutes), and then rinsed off with a high-pressure freshwater or salt-water spray. This will minimize corrosion of the material to which it is applied, which will make it especially useful for decontaminating aircraft and other equipment where corrosion is a concern. It will also minimize the time required for decontamination, which is especially advantageous for military use (on the battlefield or at fixed sites).

Saltwater can also be effectively used as the make-up water (Part D) for DF-200 formulations. The table below shows the results of kinetic tests using DF-200HF (2% PGDA/3.50% H$_2$O$_2$/4.0% Bicarbonate salt) with saltwater (~35,000 ppm total dissolved solids):

TABLE 7

Summary of the reaction rates for DF-200HF formulation (2% PGDA/3.5% H$_2$O$_2$/4.0% Bicarbonate salt) with saltwater used as the make-up water (Part D).

| | % Decontaminated | | |
|---|---|---|---|
| Simulant | 1 Minute | 15 Minutes | 60 Minutes |
| Mustard | 24 | 42 | 89 |
| G Agents | ND | ND | ND |
| VX | 62 | 96 | >99 |

Tests against the anthrax spore simulant (Bacillus globigii spores) demonstrated 99.9999% (7-Log) kill after a one-hour exposure to DF-200HF with saltwater used as the make-up water.

Surface testing was conducted with DF-200HF against the Mustard and VX simulant. For this test, 8 mg of simulant was applied to a 2" diameter test coupon made of CARC (Chemical Agent Resistant Coating). CARC is a material commonly used to paint military vehicles to protect them against chemical agent attack. After waiting one hour, the test coupon was placed in a horizontal position and covered with 1.0 g of DF-200HF (2% PGDA/3.5% H$_2$O$_2$/4.0% Bicarbonate salt). After 60 minutes, the test coupon was immersed in 25 ml of acetonitrile for 15 minutes to extract unreacted simulant from the surface. The extraction solvent (acetonitrile) was then analyzed for the unreacted simulant.

Results (shown in Table 8) demonstrate more effective decontamination of the test coupon as compared to DF-100A.

TABLE 8

Results of Surface Testing of DF-200HF on CARC.

| Decon Formulation | mg VX Simulant (Unreacted simulant on surface after 60 minutes) | Mg Mustard Simulant (Unreacted simulant on surface after 60 minutes) |
|---|---|---|
| Control | 8.0 ± 0.3 | 8.0 ± 0.3 |
| DF-100A (pH 9.2) | 2.9 | 4.5 |
| DF-200HF (2% PGDA/3.5% $H_2O_2$/4.0% Bicarb) | 1.4 | 2.5 |

DF-200HF Slurry (Kit Configurations)

Insoluble bleach activators (such as TAED, NOBS, and N-acetyl glucosamine) can be utilized in place of the (water-soluble) propylene glycol diacetate for DF-200 formulations. However, in this case, the formulation results in a slurry when mixed with water, instead of a true aqueous solution.

The present invention also provides a method to utilize a water-insoluble solid bleach activator (e.g., TAED) to produce a reactive slurry (wherein a slurry is defined as a watery mixture that includes insoluble, undissolved matter). This embodiment, designated "DF-200HF Slurry", is a modification of the DF-200HF formulation. An example of a 4-part kit configuration is shown below (amounts illustrative):

DF-200HF Slurry (4-Part Kit)

Part A (Foam Concentrate):
  20 g Variquat 80MC
  10 g Adogen 477
  4 g 1-Dodecanol
  1 g Jaguar 8000 Polymer
  5 g Di(propylene glycol) methyl ether
  7.5 g Potassium Bicarbonate
  161 g Water Part B (Solid Component):
  50 g Sodium Percarbonate
  50 g Urea Hydrogen Peroxide Part C (Bleaching Activator):
  10 g TAED (preferably encapsulated TAED, such as Warwick B637)

Part D (Make-up Water):
  800 g Water (can be freshwater or saltwater supplied at the site where use is to occur)

The formulation as described above will produce 1 liter of foam solution. The pH of the final formulation can be adjusted to be between about 9.6 and 9.8 for optimal performance. The following mixing procedure can be used: Mix Part B into Part D. Then, add Parts C and A to Parts B+D. Use, preferably, within 8 hours.

The performance against each chemical agent simulant for DF-200HF Slurry (1% TAED/3% $H_2O_2$/4% Bicarbonate salt) is shown below in Table 9:

TABLE 9

Summary of the reaction rates for the DF-200HF Slurry formulation in kinetic testing. Note that improved performance can be achieved by using higher concentrations of TAED (e.g., 2% TAED, instead of 1% TAED).

| | % Decontaminated | | |
|---|---|---|---|
| Simulant | 1 Minute | 15 Minutes | 60 Minutes |
| Mustard (HD) | 67 | 96 | ND |
| G Agents | ND | ND | ND |
| VX | 33 | 95 | ND |

The above examples of different embodiments of DF-200 would typically be used in large-scale operations where dedicated deployment equipment and a source of make-up water is readily available (e.g., for use by the military to decontaminate 'fixed sites' such as airbases and seaports), or used to minimize the volume of 'pre-packaged' water in order to minimize the weight of the formulation that needs to be shipped and stored.

DF-200 Rapid Deployment Configurations

The present invention is also of configurations emphasizing the rapid deployment of DF-200 formulations, and/or its deployment using small-scale deployment equipment (such as hand-held units, backpack units, or units mounted on small dollies). For these applications, all of the water is 'pre-packaged' into the formulation, so that no extra water is required in the field. A first example of a 3-part kit configuration for a Rapid Deployment version of DF-200HF, "DF-200HF Rapid Deployment #1", comprises (amounts illustrative):

DF-200HF Rapid Deployment #1 (3-Part Kit)

Part A (Liquid Foam Component):
  20 g Variquat 80MC
  10 g Adogen 477
  4 g 1-Dodecanol
  5 g Poly (Ethylene Oxide)
  8 g Diethylene Glycol Monobutyl Ether
  5 g Isobutanol
  45 g Potassium Bicarbonate
  approx. 19 g Potassium Hydroxide (the pH of Part A should be approximately 10.2)
  933 g Water Part B (Solid Oxidant Component):
  97 g Urea Hydrogen Peroxide Part C (Liquid Bleaching Activator):
  20 g Propylene Glycol Diacetate or Glycerol Diacetate This configuration will produce 1 liter of foam solution. The pH of the final formulation can be adjusted to be between about 9.6 and 9.8 for optimal performance. The following mixing procedure can be used: Mix Part B into Part A. After dissolution of the urea hydrogen peroxide, add Part C to Part A+B. Use, preferably, within 8.hours. The performance of DF-200HF Rapid Deployment against chemical agent simulants is shown below in Table 10:

TABLE 10

Reaction rates from kinetic testing of DF-200HF Rapid Deployment #1 configuration.

| Simulant | % Decontaminated | | |
|---|---|---|---|
| | 1 Minute | 15 Minutes | 60 Minutes |
| Mustard (HD) | 48 | 82 | ND |
| G Agents | ND | ND | ND |
| VX | 71 | 97 | >99 |

Tests against the anthrax spore simulant (Bacillus globigii spores) demonstrated 99.9999% (7-Log) kill after a 30-minute exposure to DF-200HF Rapid Deployment.

Figure 2:
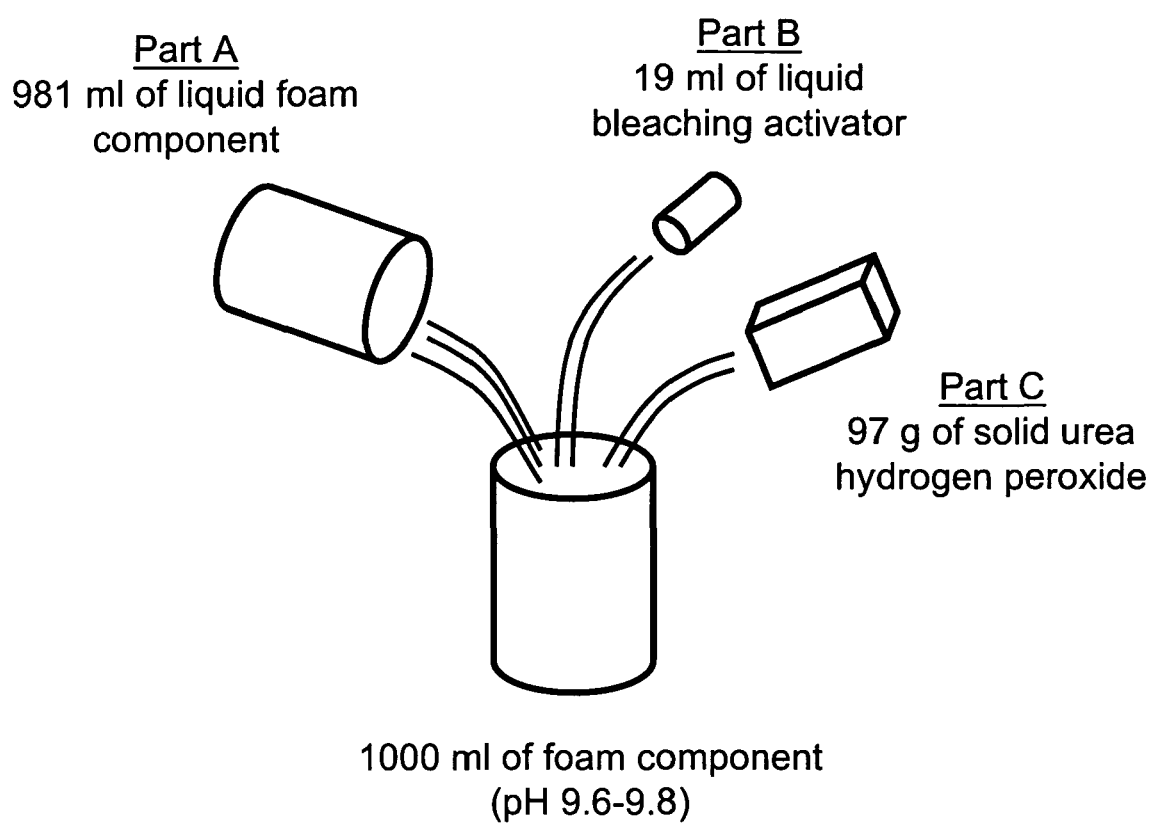
FIG. 2 is a schematic diagram of an example of a mixing procedure for "DF-200HF Rapid Deployment".

A schematic example of a preferred mixing procedure for this first example of a rapid deployment configuration of DF-200HF is shown in FIG. 2. Urea hydrogen peroxide dissolves rapidly in water. Therefore, the formulation can be prepared and deployed in a very short time at the scene of an incident involving chemical or biological warfare agents, making it ideal for use by civilian first responders (firefighters, HazMat units, police officers, and others who would be the first to arrive at the location of a CBW attack), and/or the military.

However, the particular bleaching activator (propylene glycol diacetate) used in this formulation is not stable in an aqueous solution where the pH is greater than approximately 9.9. Therefore, it is important to mix the right components in the correct order. For example, if Part C is mixed into Part A before the addition of Part B, there may be some loss of activity in DF-200HF since the propylene glycol diacetate is exposed to a solution having a pH value >9.9. This is not true, however, if Part B is added to Part A before the addition of Part C, since the addition of Part B to Part A brings the pH of the Part A+B mixture to a value below about 9.9.

The solvent, diethylene glycol monobutyl ether, used in Part A (the foam solution) of the first example shown above for DF-200HF Rapid Deployment #1 is different than the solvent that was used in the previously described DF-200HF formulation (Di(propylene glycol) methyl ether), because Di(propylene glycol) methyl ether is not stable in the high pH environment required for the foam component (Part A) in the rapid deployment configuration. Also, note that a short-chained alcohol (i.e., isobutanol) has been added to the foam component (Part A) in the rapid deployment configuration #1 of DF-200HF. While this low molecular weight alcohol can cause flammability problems in highly concentrated configurations of DF-200HF, it is not a problem in the less concentrated configurations described herein. The use of isobutanol also helps solubilize the 1-dodecanol in Part A, and improves the kinetics (chemical reactivity) of the formulation. In addition, the formulation preferably uses a different polymer, poly (ethylene oxide), than the polymer used in the other earlier described DF-200 formulations (i.e., Jaguar 8000). This alternative polymer is used because Jaguar 8000 is also not stable in the high pH environment of the liquid foam portion (Part A) of the rapid deployment formulation. Accordingly, a preferred formulation for DF-200HF Rapid Deployment #1 comprises:

DF-200HF Rapid Deployment #1

1-4% (preferably 2%) Variquat 80MC (cationic surfactant)
0.5-3% (preferably 1%) Adogen 477 (cationic hydrotrope)
0.2-0.8% (preferably 0.4%) 1-Dodecanol (fatty alcohol)
0.5-8% (preferably 0.5%) Poly (Ethylene Glycol) (polymer)
0.6-1.2% (preferably 0.8%) Diethylene Glycol Monobutyl Ether (solvent)
0-1% (preferably 0.5%) Isobutanol (short-chained alcohol)
0.1-10% (preferably 2-8%) Bicarbonate salt (buffer and peroxide activator)
0.1-10% (preferably 1-4%) Hydrogen Peroxide (oxidant)
0.1-10% (preferably 1-4%) Propylene Glycol Diacetate (bleaching activator)
52-97% Water The formulation can be adjusted to a pH value between about 9.6 and 9.8 for optimal performance, and is effective for decontamination of all target agents.

A second example of a 3-part kit configuration for a Rapid Deployment version of DF-200HF, "DF-200HF Rapid Deployment #2", comprises (amounts illustrative):

DF-200HF Rapid Deployment #2 (3-Part Kit)

Part A (Liquid Foam Component):
20 g Variquat 80MC
10 g Adogen 477
4 g 1-Dodecanol
20 g Polyethylene Glycol 8000 polymer
8 g Diethylene Glycol Monobutyl Ether
5 g Isobutanol
50 g Potassium Bicarbonate
approx. 25 g Potassium Hydroxide (the pH of Part A should be about 10.2)
933 g Water Part B (Solid Oxidant Component):
97 g Urea Hydrogen Peroxide Part C (Liquid Bleaching Activator):
20 g Propylene Glycol Diacetate or Glycerol Diacetate In this second example, Polyethylene Glycol 8000 polymer replaced the poly (Ethylene Oxide) polymer used in DF-200HF Rapid Deployment #1.

A third example of a 3-part kit configuration for a Rapid Deployment version of DF-200HF, "DF-200HF Rapid Deployment #3", comprises (amounts illustrative):

DF-200HF Rapid Deployment #3 (3-Part Kit)

Part A (Liquid Foam Component):
20 g Variquat 80MC
10 g Adogen 477
4 g 1-Dodecanol
20 g Polyethylene Glycol 8000 polymer
10 g Hexylene Glycol
45 g Potassium Carbonate
5 g Potassium Bicarbonate
700 g Water Part B (Solid Oxidant Component):
83 g Urea Hydrogen Peroxide Part C (Liquid Bleaching Activator):
20 g Glycol Diacetate (i.e., Diacetin)

In this third example, Polyethylene Glycol 8000 polymer replaced the poly (Ethylene Oxide) polymer used in DF-200HF Rapid Deployment #1 as a water-soluble polymer. Also, Hexylene Glycol replaced Diethylene Glycol Monobutyl Ether and Isobutanol used as a solvents. Finally, Glycol Diacetate (i.e., Diacetin) replaced Propylene Glycol Diacetate used as the bleaching activator. These changes in the third example were made to reduce or eliminate the use of short-chained alcohols and/or high vapor-pressure solvents to prevent possible problems with very long-term (months to years) shelf life of the liquid foam component (Part A), especially at high ambient storage temperatures, due to evaporation of the most-volatile components. Note that the combination of 45 grams of potassium carbonate and the 5 grams of potassium bicarbonate were chosen to supply both the right amount of carbonate/bicarbonate, and to adjust the pH appropriately. Alternatively, 50 grams of potassium bicarbonate could have been used (with no potassium carbonate), and then the right amount of potassium hydroxide (base) could have been added to increase the pH to the desired value, as is well known in the art.

DF-200HF Slurry Rapid Deployment

The present invention is also of a 2-part kit configuration of a rapid deployment embodiment of the DF-200HF Slurry embodiment ("DF-200HF Slurry Rapid Deployment"), in which TAED (or other solid peroxide activator) is utilized as the bleaching activator. This example of a rapid deployment configuration also requires no additional water to be added in the field (amounts illustrative):

DF-200HF-Slurry Rapid Deployment (2-Part Kit)

Part A (Liquid Foam Component):
 20 g Variquat 80MC
 10 g Adogen 477
 4 g 1-Dodecanol
 5 g Poly (Ethylene Glycol)
 8 g Diethylene Glycol Monobutyl Ether
 5 g Isobutanol
 50 g Potassium Bicarbonate
 28 g Potassium Hydroxide (the pH of Part A should be approximately 10.4)
 953 g Water Part B (Solid Oxidant and Bleaching Activator):
 97 g Urea Hydrogen Peroxide
 30 g TAED (preferably in encapsulated form, such as Warwick International B637)

This formulation will produce 1 liter of foam solution. The pH of the final formulation can be adjusted to be between 9.6 and 9.8 for optimal performance. The following procedure can be used to mix the formulation: Mix Part B into Part A. Then, wait for at least one minute before use to allow time for the TAED to react with the hydrogen peroxide. Use, preferably, within 8 hours. It is useful to note that TAED will not immediately dissolve in water, but will remain as solid particles for at least 15-20 minutes. Therefore, a filter or screen may be required so that the undissolved TAED particles will not damage or clog any pumps or other components of the deployment device. However, the formulation is ready for use approximately 1 minute after addition of the TAED particles in Part B to Part A.

It is useful to employ an encapsulated form of TAED in this configuration for two reasons. First, the protective coating (which slowly dissolves in water) will protect the TAED so that it will not react with the urea hydrogen peroxide during storage. Second, the coating will protect the TAED from the high pH conditions in Part A until the urea hydrogen peroxide dissolves and lowers the pH of the formulation to a value below approximately 9.9. TAED should be used in a similar manner as propylene glycol diacetate with respect to protecting the activator against exposure to high pH solutions. TAED will lose much of its effectiveness as a bleaching activator if it is exposed to solutions with a pH greater than 9.9. Therefore, the use of an encapsulated form of TAED will minimize its exposure to the high pH conditions immediately after Part B is mixed into Part A. The performance of DF-200HF Slurry Rapid Deployment against chemical agent simulants is given in Table 11 below.

TABLE 11

Reaction rates in kinetic testing for the DF-200HF Slurry Rapid Deployment formulation.

| | % Decontaminated | | |
|---|---|---|---|
| Simulant | 1 Minute | 15 Minutes | 60 Minutes |
| Mustard (HD) | 76 | 97 | ND |
| G Agents | ND | ND | ND |
| VX | 57 | 97 | ND |

Tests against the anthrax spore simulant (*Bacillus globigii* spores) demonstrated 99.9999% (7-Log) kill after a 30 minute exposure to DF-200HF Slurry Rapid Deployment.

Figure 3:
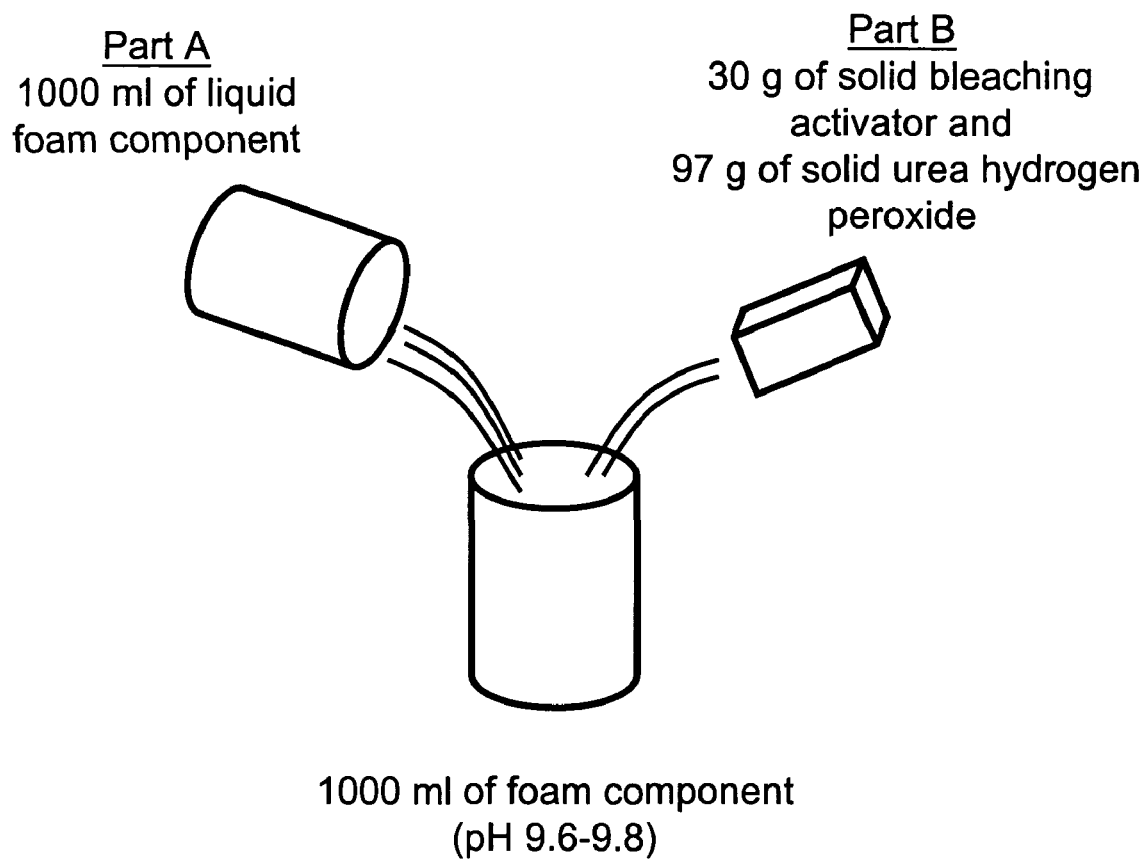
FIG. 3 is a schematic diagram of an example of a mixing procedure for another rapid deployment configuration ("DF-200HF Slurry Rapid Deployment").

A schematic illustrating an example of a process for field mixing DF-200HF Slurry Rapid Deployment is shown in FIG. 3.

The above are only a few examples of rapid deployment configurations for DF-200 formulations. As understood by one of ordinary skill in the art, other rapid deployment configurations are possible by utilizing the fundamental considerations presented in this application.

The present invention is also of a method for preparing the foam component (Part A) of the rapid deployment configurations. The following is an example of such a method:

1. Place the appropriate mass of water in a mixing vessel.
2. While stirring the water in the mixing vessel, add the bicarbonate salt. Stir until completely dissolved.
3. Slowly add the Poly (Ethylene Glycol) polymer to the mixing vessel while rapidly stirring. Be careful to avoid lumps. Stir for approximately 30 minutes, at a minimum.
4. While stirring the foam solution in the mixing vessel, add the Variquat 80MC. Stir until completely mixed.
5. While stirring the foam solution in the mixing vessel, add the Adogen 477. Stir until completely mixed.
6. Mix the diethylene glycol monobutyl ether, isobutanol, and 1-dodecanol in a separate vessel. Slowly add this mixture to the foam solution while stirring.
7. While stirring the foam solution in the mixing vessel, slowly add solid KOH until the pH reaches the appropriate value.

Alternative DF-200 Formulations

The invention is also of the following alternative DF-200 formulations:

1. An alternative formulation that includes propylene glycol to lower the freezing point of the solution;
2. An alternative formulation that utilizes sodium percarbonate as a solid source of hydrogen peroxide;
3. An alternative formulation that includes a corrosion inhibitor,
4. An alternative formulation that includes glycerol as a viscosity builder for operations such as skin decontamination;

5. An alternative formulation that utilizes O-acetyl bleaching activators, including one which is available in solid form; and 6. An alternative formulation that utilizes a bleaching activator containing a nitrile group.

DF-200 with Proplyene Glycol

The following is a first example of a 2-part kit configuration for DF-200HF that includes propylene glycol as a freeze-point depressant, and where all of the water is 'pre-packaged' in Part A, comprising (amounts illustrative):

DF-200HF Rapid Deployment with Propylene Glycol, First Example (2-Part Kit)

Part A (Liquid Foam Component):
20 g Variquat 80MC
10 g Adogen 477
20 g Poly (Ethylene Glycol) (MW 8000)
8 g Diethylene Glycol Monobutyl Ether
5 g Isobutanol
4 g 1-Dodecanol
20 g Propylene Glycol Diacetate or Glycerol Diacetate
150 g Propylene Glycol (freeze-point depressant)
approx. 6 g of 10% HCl Solution (sufficient to give a final pH of 2.5 in Part A)
777 g Water Part B (Solid Additive):
97 g Urea Hydrogen Peroxide
12 g Potassium Bicarbonate
38 g Potassium Carbonate (buffer, to adjust final pH)

This formulation will produce 1 liter of foam solution. The pH of the final formulation can be adjusted to be between about 9.6 and 9.8 for optimal performance. A person of ordinary skill in the art will understand that the ratio of potassium carbonate to potassium bicarbonate used in Part B can be adjusted to achieve the desired final pH of the formulation (preferably about 9.6 to about 9.8). Hence, in this example, the potassium carbonate serves as both a base and a source of carbonate/bicarbonate. To prepare this formulation, mix Part B into Part A. Use, preferably, within 8 hours. The performance of this first example of DF-200HF with propylene glycol against chemical agent simulants is shown in Table 12.

TABLE 12

Reaction rates from kinetic testing for DF-200HF with propylene glycol (first example).

| | % Decontaminated | | |
|---|---|---|---|
| Simulant | 1 Minute | 15 Minutes | 60 Minutes |
| Mustard (HD) | 16 | 80 | ND |
| G Agents | ND | ND | ND |
| VX | 66 | 90 | >99 |

Tests against the anthrax spore simulant (Bacillus globigii spores) demonstrated 99.9999% (7-Log) kill after a 30-minute exposure to DF-200HF with propylene glycol (first example).

When all of the water is "pre-packaged" in Part A, the mixing of the formulation for use can be accomplished in a very short time since it only consists of two parts. Therefore, it could be deployed very rapidly at the scene of an incident involving chemical and biological warfare agents. This configuration is ideal for use the civilian first responder (firefighter, HazMat units, police officers, and others who would be the first to arrive at the location of a CBW attack). However, it is heavier to carry than other configurations that add water in the field.

This configuration also incorporates the bleaching activator, propylene glycol diacetate, into the foam component Part A (rather than storing it as a separate, third component). This is possible because the pH of the foam component is less than 3. Propylene glycol diacetate will hydrolyze in solutions of pH greater than 3, but is hydrolytically stable in solutions of pH less than 3. This configuration also uses the polyethylene glycol polymer (PEG 8000) for viscosity enhancement. This polymer is used in many cosmetics and is extremely soluble and stable in water. In addition, it is easier to mix into solution than Jaguar 8000 or a high molecular weight poly(ethylene oxide), since it does not have the tendency to clump.

This configuration includes propylene glycol as a freeze-point depressant. Propylene glycol is considered to be an environmentally friendly antifreeze. In this case, the concentration is approximately 15% by weight, which lowers the freezing point of Part A to approximately −20° C. This configuration has also been tested with good results with propylene glycol concentrations as high as 40% by weight.

An alternative to the first example of DF-200HF with Proplyene Glycol shown above is to use sodium percarbonate as the source of the bicarbonate and as a portion of the peroxide in Part B, instead of using urea hydrogen peroxide. This substitution is useful because sodium percarbonate is much less expensive than urea hydrogen peroxide. This second example of DF-200HF with Proplyene Glycol is shown below (amounts illustrative):

DF-200HF Rapid Deployment with Propylene Glycol, Second Example (2-Part Kit)

Part A (Liquid Foam Component):
20 g Variquat 80MC
10 g Adogen 477
20 g Poly (Ethylene Glycol) (MW 8000)
8 g Diethylene Glycol Monobutyl Ether
5 g Isobutanol
4 g 1-Dodecanol
20 g Propylene Glycol Diacetate or Glycerol Diacetate
150 g Propylene Glycol (freeze-point depressant)
approx. 6 g of 10% HCl Solution (sufficient to give a final pH of 2.5 in Part A)
777 g Water Part B (Solid Additive):
90 g Sodium Percarbonate
15 g Citric Acid (buffer, to adjust final pH)

This formulation will produce 1 liter of foam solution. The pH of the final formulation can be adjusted to be between about 9.6 and 9.8 for optimal performance. The following mixing procedure can be used: Mix Part B into Part A. Use, preferably, within 8 hours. Alternatively, sodium bisulfate (a common pool conditioning chemical), or other acid, can be used in place of citric acid to adjust the pH. The performance of this second example of DF-200HF with Proplyene Glycol (utilizing sodium percarbonate) against chemical agent simulants is shown in Table 13.

TABLE 13

Reaction rates from kinetic testing for the second example of DF-200HF with propylene glycol (utilizing sodium percarbonate).

| | % Decontaminated | | |
|---|---|---|---|
| Simulant | 1 Minute | 15 Minutes | 60 Minutes |
| Mustard (HD) | 80 | ND | ND |
| VX | 76 | 96 | >99 |

In general, sodium percarbonate dissolves much more slowly than urea hydrogen peroxide after it has been added to Part A. However, to increase the dissolution velocity, sodium percarbonate can be milled to approximately a 100-mesh size for use in this configuration. The time to dissolve the sodium percarbonate was decreased from approximately 30 minutes to about 2 minutes when milled sodium percarbonate was used.

DF-200 with Corrosion Inhibitor

Corrosion inhibitors can be added to DF-200 formulations to reduce their corrosivity. A preferred corrosion inhibitor for use in DF-200 formulations is N,N-dimethyl ethanolamine. However, other corrosion inhibitors, such as triethanolamine, ethanolamine salts of C9, C10, and C12 diacid mixtures, dicyclohexyl amine nitrite, and N,N-dibenzylamine, can be used. The Corrosion inhibitors added to DF-200 formulations can serve multiple purposes:

1. a corrosion inhibitor,
2. a pH buffer,
3. a solvent to keep 1-dodecanol in solution, and
4. a co-solvent to solubilize insoluble chemical agents, such as sarin or mustard.

An example of a 3-part kit configuration of DF-200HF with a corrosion inhibitor comprises (amounts illustrative):

DF-200HF Rapid Deployment with Corrosion Inhibitor (3-Part Kit)

Part A (Liquid Foam Component):
  20 g Variquat 80MC
  10 g Adogen 477
  4 g 1-Dodecanol
  5 g Poly (Ethylene Glycol)
  10 g N,N-dimethyl ethanolamine (corrosion inhibitor)
  50 g Potassium Bicarbonate
  approx. 18 g Potassium Hydroxide (suff. to give a final pH of 10.2 in Part A)
  936 g Water Part B (Solid Oxidant Component):
  97 g Urea Hydrogen Peroxide Part C (Liquid Bleaching Activator):
  20 g Propylene Glycol Diacetate or Glycerol Diacetate This formulation will produce 1 liter of foam solution. The pH of the final formulation can be adjusted to be between about 9.6 and 9.8 for optimal performance. The following mixing procedure can be used: Mix Part B into Part A. Then, after dissolution of the urea hydrogen peroxide, add Part C to Part A+B. Use, preferably, within 8 hours. The performance of DF-200HF with corrosion inhibitor is shown below against chemical agent simulants is given in Table 14.

TABLE 14

Reaction rates in kinetic testing for DF-200HF with a corrosion inhibitor.

| | % Decontaminated | | |
|---|---|---|---|
| Simulant | 1 Minute | 15 Minutes | 60 Minutes |
| Mustard (HD) | 7 | 41 | 79 |
| VX | 58 | 94 | 99 |

Tests against the anthrax spore simulant (*Bacillus globigii* spores) demonstrated 99.9999% (7-Log) kill after a 60-minute exposure to DF-200HF with a corrosion inhibitor. The addition of the corrosion inhibitor has a detrimental effect on the performance of DF-200 against chemical agents, but has no measured effect on the performance of DF-200HF against biological agents. Similar results were obtained when an alternative corrosion inhibitor, 1% triethanolamine, was used.

DF-200 with Glycerol

In another embodiment of a DF-200 formulation, glycerol may be employed as a viscosity builder in place of Jaguar 8000, poly (ethylene oxide), or polyethylene glycol. Glycerol is a common ingredient in cosmetics, where it is used a viscosity builder, as well as a solvent, humectant and emollient. Thus, the use of glycerol in DF-200 formulations can serve multiple purposes:

1. Viscosity builder,
2. a humectant (i.e., a substance which moisturizes the skin),
3. a solvent to keep 1-dedecanol in solution, and
4. a co-solvent to solubilize insoluble chemical agents, such as sarin or mustard.

An example of a 3-part kit configuration of DF-200HF with glycerol comprises (amounts illustrative):

DF-200HF Rapid Deployment with Glycerol (3-part Kit)

Part A (Liquid Foam Component):
  20 g Variquat 80MC
  10 g Adogen 477
  4 g 1-Dodecanol
  40 g Glycerol (viscosity builder)
  40 g Potassium Bicarbonate
  about 17 g Potassium Hydroxide (sufficient to give a final pH of 10.2 in Part A)
  906 g Water Part B (Solid Oxidant Component):
  97 g Urea Hydrogen Peroxide Part C (Liquid Bleaching Activator):
  20 g Propylene Glycol Diacetate or Glycerol Diacetate This formulation will produce 1 liter of foam solution. The pH of the final formulation can be adjusted to be between about 9.6 and 9.8 for optimal performance. The following mixing procedure can be used: Mix Part B into Part A. Then after dissolution of the urea hydrogen peroxide, add Part C to Part +/B. Use, preferably, within 8 hours. The performance of DF-200HF with glycerol against chemical agent simulants is given in Table 15.

TABLE 15

Reaction rates in kinetic testing for DF-200HF with glycerol.

| | % Decontaminated | | |
|---|---|---|---|
| Simulant | 1 Minute | 15 Minutes | 60 Minutes |
| Mustard (HD) | 63 | 96 | ND |
| G Agents | ND | ND | ND |
| VX | 76 | 99 | ND |

Tests against the anthrax spore simulant (*Bacillus globigii* spores) demonstrated 99.9999% (7-Log) kill after a 30-minute exposure to DF-200HF with glycerol.

This formulation can be used for direct application to humans because the glycerol will act as a humectant. This formulation could also be utilized, e.g., as a spray or shower, by removing foaming constituents (such as 1-dodecanol and Adogen 477), and by reducing the concentration of peroxide. However, a drawback to the use of glycerol is that it is solid at a fairly high temperature (below about 10° C.). Therefore, it would preferably be used in controlled temperature conditions (i.e., warm temperature conditions).

Propylene glycol diacetate, a bleaching activator used in many of the previously described DF-200 configurations is not presently available in solid form. However, other bleaching activators are available in solid form.

DF-200 with Acetylcholine Chloride

Solid O-acetyl bleaching activators (e.g., acetylcholine chloride, which is often used in eye drop solutions) can be used in DF-200 formulations in place of (liquid) propylene glycol diacetate. The chemical structure of this O-acetyl bleaching activator is shown below. As can be seen, the molecule contains an O-acetyl group that can activate peroxide, and it is a quaternary compound, which is very compatible with DF-200 formulations. Acetylcholine chloride is also soluble in water and is very hygroscopic.

$$CH_3-\overset{O}{\underset{\|}{C}}-OCH_2CH_2-\overset{CH_3}{\underset{CH_3}{\overset{|}{N^+}}}-CH_3 \quad Cl^-$$

An example of a 2-part kit configuration of DF-200HF using acetylcholine chloride comprises (amounts illustrative):

DF-200HF Rapid Deployment Using Acetylcholine Chloride (2-Part Kit)

Part A (Liquid Foam Component):
  20 g Variquat 80MC
  10 g Adogen 477
  30 g Poly (Ethylene Glycol) (MW 8000)
  8 g Diethylene Glycol Monobutyl Ether
  5 g Isobutanol
  4 g 1-Dodecanol
  150 g Propylene Glycol
  50 g Potassium Bicarbonate
  approx. 17 g Potassium Hydroxide (suff. to give a final pH of 10.2 in Part A)
  803 g Water Part B (Solid Additive):
  97 g Urea Hydrogen Peroxide
  25 g Acetycholine Chloride (solid bleaching activator)

This formulation will produce approximately 1 liter of foam solution. The pH of the final formulation can be adjusted to be between about 9.6 and 9.8 for optimal performance. To use this formulation, mix Part B into Part A. Use, preferably, within 8 hours. The performance of DF-200HF using acetylcholine chloride against chemical agent simulants is shown in Table 16.

TABLE 16

Reaction rates from kinetic testing for the DF-200HF using acetylcholine chloride as an activator.

| | % Decontaminated | | |
|---|---|---|---|
| Simulant | 1 Minute | 15 Minutes | 60 Minutes |
| Mustard (HD) | 60 | 98 | ND |
| VX | 10 | 85 | >99 |

Tests against the anthrax spore simulant (Bacillus globigii spores) demonstrated 99.9999% (7-Log) kill after a 30-minute exposure to DF-20OHF using acetylcholine chloride.

Two other O-acetyl bleaching activators, monoacetin (glycerol monoacetate) and diacetin (glycerol diacetate), have also been tested for their effectiveness in DF-200 formulations. Both of these compounds have also proven to be extremely effective bleaching activators. These compounds are water-soluble liquids.

Experiments have also shown that the peroxide in DF-200 formulations is also effectively activated by a nitrile-containing compound, such as 4-cyanobenzoic acid (which is water-soluble), at a concentration of, for example, 2%, for the neutralization of both chemical agent and biological agent simulants.

DF-200 Using Peracetic Acid

Tests were conducted using peracetic acid as the oxidant in DF-200, instead of hydrogen peroxide. The following formulation was used:
  2% Variquat 80MC (cationic surfactant)
  2% peracetic acid (oxidant)
  5% potassium bicarbonate (buffer and activator)
  91% water The pH was adjusted to 9.8 with solid KOH and the formulation was tested against the simulants for mustard, VX, and anthrax spores. The performance of this formulation is shown in Table 17 against chemical agent simulants.

TABLE 17

Reaction rates in kinetic testing for DF-200 with 2% peracetic acid.

| | % Decontaminated | | |
|---|---|---|---|
| Simulant | 1 Minute | 15 Minutes | 60 Minutes |
| Mustard (HD) | 27 | 58 | 68 |
| VX | 68 | 76 | 95 |

Tests against the anthrax spore simulant (*Bacillus globigii* spores) demonstrated 99.9999% (7-Log) kill after a 30-minute exposure to DF-200 with 2% peracetic acid.

Tests were also conducted for DF-200 using a higher concentration of peracetic acid (3.5%) in the following formulation:

2% Variquat 80MC (cationic surfactant)
3.5% peracetic acid (oxidant)
5% potassium bicarbonate (buffer and activator)
89.5% water The pH was adjusted to 9.8 with solid KOH and the formulation was tested against the simulants for mustard, VX, and anthrax spores. The performance of this formulation is shown in Table 18 against chemical agent stimulants.

TABLE 18

Reaction rates in kinetic testing for DF-200 with 3.5% peracetic acid.

| | % Decontaminated | | |
|---|---|---|---|
| Simulant | 1 Minute | 15 Minutes | 60 Minutes |
| Mustard (HD) | 40 | 94 | ND |
| VX | 74 | 96 | 98 |

The results show that use of peracetic acid as an alternative oxidant is effective against chemical agent simulants, but is not as effective as DF-200 formulations using activated hydrogen peroxide (i.e., the combination of hydrogen peroxide, bicarbonate, and propylene glycol diacetate) as the oxidant. However, the DF-200 formulations with 2-3.5% peracetic acid are very effective for spore kill. Nevertheless, use of this oxidant is not as attractive as hydrogen peroxide because peracetic acid is not presently available in a safe, convenient solid form, and the shelf life of the liquid form is rather short.

Tests were also conducted to determine the minimum constituents required for spore kill in a DF-200 formulation that utilizes peracetic acid as an oxidant. These results indicate that only three constituents, i.e., peracetic acid, bicarbonate and the cationic surfactant, are necessary to achieve high rates of spore kill.

Live Agent Tests Using DF-200HF

Live agent tests on three chemical agents (soman ("GD"), VX, and mustard ("HD")) and two biological agents (anthrax spores and Yersinia pestis) were conducted. The results of kinetic testing of DF-200HF (using a three-part configuration) on the chemical agents are shown in Table 19.

TABLE 19

Reaction rates in kinetic testing for DF-200HF against chemical agents.

| | % Destruction of Chemical Agent at Time Interval | | |
|---|---|---|---|
| Chemical Agent | 1 minute | 15 minutes | 60 minutes |
| GD | 99.98 ± 0.01 | 99.97 ± 0.01 | 99.98 ± 0.01 |
| VX | 91.20 ± 8.56 | 99.80 ± 0.08 | 99.88 ± 0.04 |
| HD | 78.13 ± 10.53 | 98.46 ± 1.43 | 99.84 ± 0.32 |

After exposure of GD to DF-200HF, methylphosphonic acid (MPA) and pinacolyl methylphosphonic acid (PMPA) were identified as byproducts. After exposure of VX to DF-200HF, ethyl methylphosphonic acid (EMPA) and MPA were identified as byproducts. This indicated that the destruction of the VX followed the more desirable path to the phosphonic acids, rather than to EA2192 (a toxic byproduct which can also be produced during VX degradation). Lastly, after exposure of HD to DF-200HF, the initial degradation products for HD comprised a mixture of the sulfoxide and sulfone byproducts, followed later by nearly complete disappearance of each of these byproducts after 60 minutes.

Results of tests against anthrax spores is shown in Tables 20 and 21 and against Yersinia pestis (i.e., the plague bacterium) are shown in Table 22 (NG refers to 'no growth'). The detection limit for these tests was 10 CFU/ml. Note that the 'error bars' in the '% Reduction' column takes into account this detection limit.

TABLE 20

Kill rates for B. anthracis AMES-RIID spores in a solution of DF-200HF.

| B. anthracis AMES-RID | Average CFU/ml | Log Reduction | % Reduction |
|---|---|---|---|
| Control | 1.21E+07 | 0 | 0.00 |
| 15 min contact | NG | 7 | 100 ± .00004 |
| 30 min contact | NG | 7 | 100 ± .00004 |
| 60 min contact | NG | 7 | 100 ± .00004 |

TABLE 21

Kill rates for B. anthracis ANR-1 spores in a solution of DF-200HF.

| B. anthracis ANR-1 | Average CFU/ml | Log Reduction | % Reduction |
|---|---|---|---|
| Control | 6.42E+07 | 0 | 0/00 |
| 15 min contact | NG | 7 | 100 ± .00004 |
| 30 min contact | NG | 7 | 100 ± .00004 |
| 60 min contact | NG | 7 | 100 ± .00004 |

TABLE 22

Kill rates for Y. pestis cells in a solution of DF-200HF.

| Y. pestis (ATCC 11953) | Average CFU/ml | Log Reduction | % Reduction |
|---|---|---|---|
| Control | 1.33E+07 | 0 | 0.00 |
| 15 min contact | NG | 7 | 100 ± .00004 |
| 30 min contact | NG | 7 | 100 ± .00004 |
| 60 min contact | NG | 7 | 100 ± .00004 |

The petri dishes used for cell growth on each of these tests were saved for 21 days following the tests to verify that DF-200HF had actually killed the spores, rather than just inhibiting their growth. No growth on any of the petri dishes was observed after the 21-day period.

Toxic Industrial Chemicals Tests Using DF-200HF

Several toxic industrial chemicals (TICs) have also been tested against DF-200HF. A summary of the TICs tested to date and the results of those tests is shown in Table 23. Note that the results for malathion, butyl isocyanate, sodium cyanide, and carbon disulfide were obtained by analyzing for the unreacted chemical in foam solution, while the results for phosgene was obtained by analyzing for the chemical in the headspace above a foam solution. These results demonstrate very effective neutralization of these toxic industrial chemicals.

TABLE 23

Summary of Toxic Industrial Chemical (TIC) Neutralization Tests with DF-200HF.

| TIC | % Decontaminated | | |
|---|---|---|---|
| | 1 minute | 15 minutes | 160 minutes |
| Malathion (liquid) | 89 | 95 | Below |
| Hydrogen Cyanide (gas) | >99 | >99 | >99 |
| Sodium Cyanide (solid) | 93 | 98 | >99 |
| Butyl Isocyanate (liquid) | 99 | Below | Below |
| Carbon Disulfide (liquid) | >99 | >99 | Below |
| Phosgene (gas) | 98 | >99 | >99 |

The preceding examples can be repeated with similar success by substituting the generically or specifically described reactants and/or operating conditions of this invention for those used in the preceding examples.

DF-200 With Sorbent Material Added to "Dry Out" Liquid Ingredients

According to the present invention, a water-soluble, highly adsorbent additive is used to "dry out" one or more liquid ingredients of the family of DF-200 decontamination formulations, such as the liquid bleaching activator (i.e., peroxide activator) that is used for the "Part C" component of a multi-part, kit configuration (e.g., 3-part or 4-part configuration). A goal of "drying out" the liquid bleaching activator(s) is to produce a dry, free-flowing powder that can be placed in protective packaging with a desiccant, have an extended shelf life, be more convenient to handle and mix in the field (as compared to handling and mixing a liquid), and not leave a residue. In this way, the sorbent material acts as a drying agent.

The process of "drying out" the liquid bleaching activator (e.g., propylene glycol diacetate or glycerol diacetate) is not really an evaporation process as it is commonly understood. Rather, the present invention uses a sorbent additive that absorbs and/or adsorbs (i.e., at room temperature) substantially all of the liquid activator to produce a powdered, free-flowing product that is easier to handle. The sorbent additive preferably does not contain any water, since most of the bleaching activators will hydrolyze or degrade in the presence of moisture. Also, the sorbent additive preferably should be water-soluble, so that it can be rapidly dissolved and mixed, and leave no residue.

Alternatively, an insoluble sorbent additive may be used (e.g., Cabosil), depending on the application, if the presence of insoluble particles in the formulation is acceptable. For example, insoluble sorbent particles may be used as a cleaning solution and/or where an abrasive effect is desired. Also, for some methods of application, the presence of a sludge at the bottom of a container may not be a problem. However, the presence of insoluble sorbent particles in the decontamination formulation may damage a pump mechanism, clog a spray nozzle, or leave an undesirable residue.

The sorbent additive is preferably finely ground to a small particle size so that a large effective surface area can be provided for adsorbing/absorbing the liquid activator. The sorbent additive preferably is chemically compatible with the DF-200 formulation, and should not cause degradation of the foaming properties and/or decontamination effectiveness. The sorbent additive may be selected from elements/ingredients already found in the DF-200 decontamination formulation. The sorbent additive may comprise a single powder, or a blend of different powders of different materials. For example, in some foaming embodiments of DF-200, Polyethlyene Glycol 8000 (PEG 8000 or Carbowax 8000) is used as a viscosity builder. Since the PEG 8000 used in the formulation presented herein is typically provided as a fine powder, and is essentially anhydrous, then it can also serve as some (or all) of the sorbent additive for "drying out" the liquid bleaching activator component.

Suitable compounds that may be used as the sorbent additive, either alone or in various combinations, according to the present invention, include, but are not limited to:

| | |
|---|---|
| Sodium hexa meta phosphate | $(NaPO_3)_6$ |
| Sodium ortho phosphate | $Na_3PO_4$ |
| Sodium mono hydrogen ortho phosphate | $Na_2HPO_4$ |
| Sodium acid pyro phosphate | $Na_4P_2O_7$ |
| Sodium tri-polyphosphate | $Na_5P_3O_{10}$ |
| Sodium sulfate | $Na_2SO_4$ (fine grind) |
| Sodium carbonate | $Na_2CO_3$ (or bicarbonate) |
| Calcium meta phosphate | $Ca(PO_3)_2$ |
| Calcium hypo chlorite | $Ca(ClO)_2$ |
| Calcium chloride | $CaCl_2$ |
| Calcium carbonate | $CaCO_3$ |
| Potassium bicarbonate | $KHCO_3$ |
| Potassium bromide | KBr |
| Potassium carbonate | $K_2CO_3$ |
| Zeolytes | |
| Precipitated Silicas | |
| Percarbonates | |
| Sodium Citrate | |
| Dendritic Salt (i.e., sea salt) | |
| Citric Acid | |
| Potassium Bromide | |
| Polyethylene Glycols, PEG 8000 | |
| Urea | |
| Polyols (e.g., Sorbitol, Mannitol) | |

Examples of suitable polyols that may be used as the sorbent additive of the present invention include, but are not limited to:
  Sorbitol,
  Mannitol,
  Hydrogenated Starch Hydrolysates (HSH),
  Maltitol,
  Zylitol,
  Lactitol Monohydrate,
  Anhydrous Isomalt,
  Erythritol, and
  Polydextrose.

The polyols listed above are sugar-free sweeteners. They are carbohydrates, but they are not sugars. Chemically, polyols are considered polyhydric alcohols or "sugar alcohols" because part of the structure resembles sugar and part is similar to alcohols. However, these sugar-free sweeteners are neither sugars nor alcohols, as those word are commonly used. They are derived from carbohydrates whose carbonyl group (e.g., aldehyde or ketone, reducing sugar) has been reduced to a primary or secondary hydroxyl group.

The most widely used polyols in the food industry are sorbitol, mannitol, and malitol. Sorbitol is derived from glucose; mannitol from fructose; and malitol from high maltose corn syrup. Sorbogem™ and Mannogem™ are product names for sorbitol and mannitol sold by SPI Polyols, Inc., and are available in a wide range of particle size, down to fine sizes (i.e., Sorbogem Fines™).

Sorbitol is a hexahydric alcohol ($C_6H_{14}O_6$) corresponding to glucose, and has a molecular weight of 182.2. It occurs naturally, and is also produced by the hydrogenation of glucose syrup in the presence of Raney Nickel Catalyst. Some synonyms for sorbitol include: cholaxine, clucitol, diakarmon, gulitol, 1-gulitol, karion, nivitin, sionit, sorbicolan, sorbite, d-sorbitol, sorbo, sorbol, sorbostyl, sorvilande. Sorbitol has a CAS No. 50-70-4 and an EC No. 200-061-5.

The sorbent additive may be selected to be a "G.R.A.S." material, meaning that it is Generally Accepted As Safe to be used in this and other applications.

An example of a 3-part kit configuration of a "high foam", rapid deployment version of a DF-200 formulation with a sorbent material added to the liquid bleaching activator component, according to the present invention, is:

Rapid Deployment DF-200HF with Sorbent Additive (no Additional Water Required)

Part A (Liquid Foam Component):
  20 g Variquat 80MC
  10 g Adogen 477
  4 g 1-Dodecanol
  8 g Diethylene Glycol Monobutyl Ether
  5 g Isobutanol
  50 g Potassium Bicarbonate
  18 g Potassium Hydroxide (the pH of Part A should be approximately 10.4)
  933 g Water
Part B (Solid Oxidant Component):
  97 g Urea Hydrogen Peroxide
Part C (Powdered Peroxide Activator):
  20 g Propylene Glycol Diacetate or Glycerol Diacetate
  40 g Sorbitol (Sorbigem Fines)
  20 g Polyethylene Glycol 8000 (Carbowax 8000)

Note: This formulation as described above will produce 1 liter of foam solution. The pH of the final formulation should be between 9.6 and 9.85. To prepare this formulation, use the following procedure: Mix Part B and Part C into Part A. After dissolution, use within 8 hours.

The performance of DF-200HF with Sorbent Additive in the configuration shown above for neutralization of chemical agent simulants is given in Table 24 below:

TABLE 24

Performance Results of DF-200HF with Sorbent Additive

| Simulant | % Decontaminated | | |
|---|---|---|---|
| | 1 Minute | 15 Minutes | 60 Minutes |
| Mustard (HD) | 61 | 91 | Not Detected |
| VX | 28 | 92 | >99 |

Additionally, tests against the anthrax spore simulant (*Bacillus globigii* spores) demonstrated 99.9999% (7-log) kill after a 60-minute exposure to DF-200HF with Sorbent Additive.

Many different methods may be used to prepare the Part C component. In one example, the method may comprise performing the following steps:
1) place the sorbent additive (e.g., sorbitol powder) in a mixing vessel;
2) while mixing, slowly add the liquid peroxide activator (e.g., propylene glycol diacetate or glycerol diacetate). Mix until a fine powder (no lumps) is achieved;
3) while continuing to mix, slowly add the polyethylene glycol 8000; and
4) let dry for approximately 24 hours. Re-mix to break up any lumps that have formed.

The order of these steps may be reversed, or combined in any permutation.

Figure 4:
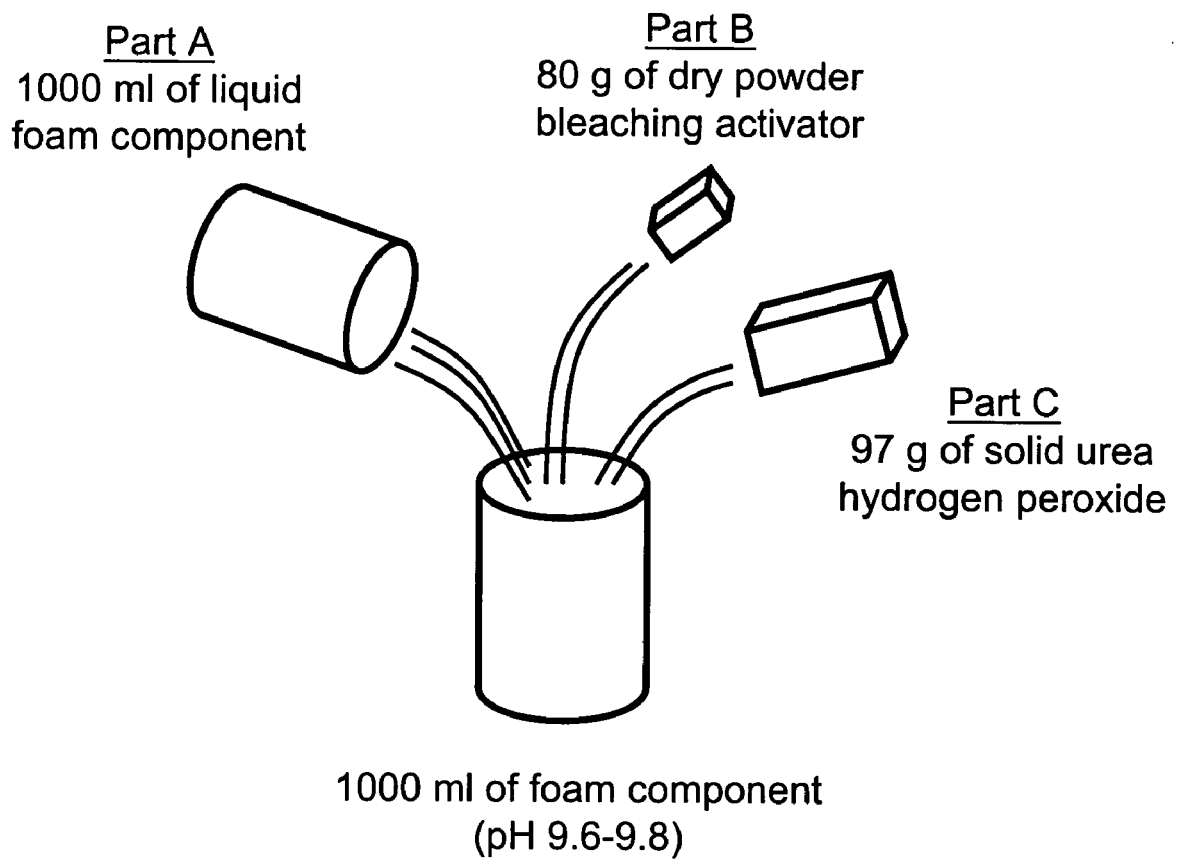
FIG. 4 is a schematic diagram of an example of a mixing procedure for "DF-200HF Rapid Deployment", according to the present invention, where Part B includes a sorbent additive.

FIG. 4 is a schematic diagram of an example of a mixing procedure for "DF-200HF Rapid Deployment with Sorbent Additive", according to the present invention, where Part B includes a sorbent additive that has been used to "dry out" the liquid peroxide activator component.

An alternative configuration for Part C of the example shown above for a high foam", rapid deployment version of a DF-200 formulation with a sorbent material comprises:
  60 g Mannitol (Mannigem™),
  20 g PEG 8000, and
  20 g Diacetin.

Still another alternative configuration of Part C comprises:
  20 g Dendritic Salt,
  20 g Citric Acid,
  40 g PEG 8000, and
  20 g Diacetin.

In the example of DF-200HF with Sorbent Additive shown above, the amount of sorbent added (e.g., 40 g of sorbitol/SORBIGEM™) is approximately equal to the amount of the other two ingredients (20 g of propylene glycol diacetate and 20 g of polyethylene glycol 8000). This represents approximately the minimum amount of sorbitol that needs to be added in order for the Part C component to become a freely flowing powder. Note also that the 20 g of polyethylene glycol 8000 is included here in Part C, whereas before it was included in Part A (see, e.g., the earlier referenced version designated "DF-200HF Rapid Deployment #3 (3-part kit)"). The reason for moving the 20 g of polyethylene glycol (PEG) 8000 from Part A to Part C is because PEG 8000 is also a powder that acts as a sorbent material to sorb the liquid bleaching agent. Hence, PEG 8000 effectively acts as a co-sorbent, in addition to sorbitol. Since PEG 8000 is used as a water-soluble polymer to add viscosity to the foam solution, moving it from Part A to Part C allows it to be used as a co-sorbent, thereby reducing the total amount of Sorbitol needed to achieve the same result, i.e., a freely flowing powdered peroxide activator.

Alternatively, since sorbitol also adds viscosity to the DF-200 formulation, it may be possible to increase the amount of sorbitol added (i.e., beyond 40 g), while reducing the amount of PEG 8000 added (i.e., less than 20 g). Conversely, the amount of PEG 8000 added may be increased, while reducing the amount of sorbitol added.

In a non-foaming version of DF-200, i.e., DF-200NF, the formulation does not have any water-soluble polymer additives (because no foam is being produced when the product is applied). In this case, the minimum amount of sorbent material that needs to be added to "dry out" the liquid peroxide activator component will likely need to be more (possibly about 50% more, i.e., 60 g of sorbitol per 20 g of liquid peroxide activator), since there is no PEG 8000 viscosity additive acting as a co-sorbent.

In another embodiment of the present invention, a DF-200 formulation with sorbent additive may comprise:
  1-10% benzalkonium chloride;
  1-8% propylene glycol diacetate or glycerol diacetate;
  1-16% hydrogen peroxide;
  2-8% potassium bicarbonate;
  a sufficient amount of sorbitol or mannitol such that a freely flowing powder results when the sorbitol or mannitol is mixed with the 1-8% propylene glycol diacetate or glycerol diacetate; and balance water.

In this example, a sufficient amount of sorbent additive may be about 1-4%.

In many of the DF-200 formulations, the Part B component consists of solid (i.e., powdered) urea hydrogen peroxide (UHP). In the present invention, we have used a sorbent additive to "dry out" the liquid peroxide activator component (Part C), and turn it into a freely flowing powder. It would be possible to pre-mix the powders from Parts B and C prior to use. However, there is a concern that small amounts of water released by the gradual degradation of the UHP over time could attack or otherwise damage the ingredients in (powdered) Part C. For this reason, a preferred embodiment of the present invention is to store Parts B and C (both in powdered form) in separate containers (e.g., plastic bags) with desiccants. However, it may be possible to encapsulate the powered activator component (Part C) in a protective coating that would permit pre-mixing of parts B and C for an extended period of time (such as is presently done with the encapsulated TAEDS or NOBS bleaching activators for laundry detergents).

Although the invention has been described in detail with particular reference to these preferred embodiments, other embodiments can achieve the same results. In particular, the sorbent additive may also be added to other components of kit configurations, for example, adding the sorbent additive to Part A (liquid foam component) or to Part B (liquid oxidizer component), in order to "dry out" those components. Additionally, the sorbent additive may be added, where appropriate, to any of the examples and embodiments of DF-100 and DF-200 decontamination formulations disclosed anywhere within this application.

Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A formulation for use in neutralization of a toxant, said formulation comprising:
    a cationic surfactant;
    a reactive compound comprising one or more compounds selected from the group consisting of hydrogen peroxide, urea hydrogen peroxide, hydroperoxycarbonate, peracetic acid, sodium perborate, sodium peroxypyrophosphate, sodium peroxysilicate, and sodium percarbonate;
    a bleaching activator selected from the group consisting of O-acetyl, N-acetyl and nitrile group bleaching activators;
    1-4% by weight of a polyol sorbent additive selected from the group consisting of sorbitol, mannitol, hydrogenated starch hydrolysates, maltitol, zyiltol, lactitol monohydrate, anhydrous isomalt, erthritol, polydextrose and combinations thereof; and
    a carbonate or bicarbonate salt;
    wherein said cationic surfactant, said reactive compound, said bleaching activator, said sorbent additive, and said carbonate or bicarbonate salt, when mixed with water and exposed to the toxant, neutralizes the toxant.

2. The formulation according to claim 1, wherein said cationic surfactant comprises a quaternary ammonium salt selected from the group consisting of cetyltrimethyl ammonium bromide, benzalkonium chloride, benzethonium chloride, cetylpyridinium chloride, alkyldimethylbenzylammonium salt, tetrabutyl ammonium bromide, and a mixture of benzyl (C12-C16) alkyldimethylammonium chlorides, and combinations thereof.

3. The formulation according to claim 1, further comprising a water-soluble polymer selected from the group consisting of polyvinyl alcohol, guar gum, (cationic or nonionic) polydiallyl dimethyl ammonium chloride, polyacrylamide, poly (ethylene oxide), glycerol, polyethylene glycol 8000 (PEG 8000), and guar gum 2-hydroxypropyl ether, and combinations thereof.

4. The formulation according to claim 1, further comprising a fatty alcohol comprising from 8 to 20 carbon atoms per molecule.

5. The formulation according to claim 1, further comprising a solvent selected from the group consisting of Di(propylene glycol) methyl ether, diethylene glycol monobutyl ether, and combinations thereof.

6. The formulation according to claim 1, wherein the carbonate or bicarbonate salt is selected from the group consisting of potassium bicarbonate, sodium bicarbonate, ammonium bicarbonate, ammonium hydrogen bicarbonate, lithium bicarbonate, ammonium carbonate, and potassium carbonate, and combinations thereof.

7. The formulation according to claim 1, wherein said bleaching activator comprises one or more water-soluble bleaching activators selected from the group consisting of acetyrcholine chloride, 4-cyanobenzoic acid, ethylene glycol diacetate, propylene glycol monomethyl ether acetate, methyl acetate, dimethyl glutarate, diethylene glycol monoethyl ether acetate, glycerol diacetate (Diacetin), glycerol monoacetate, glycerol triacetate, and propylene glycol diacetate, and combinations thereof.

8. The formulation of claim 7, wherein the bleaching activator is selected from the group consisting of acetylcholine chloride, 4-cyanobenzoic acid, propylene glycol monomethyl ether acetate, methyl acetate, dimethyl glutarate, diethylene glycol monoethyl ether acetate, glycerol diacetate (Diacetin), glycerol monoacetate, and propylene glycol diacetate, and combinations thereof.

9. The formulation of claim 8, wherein the bleaching activator is acetylcholine chloride or 4-cyanobenzoic acid.

10. The formulation according to claim 1, wherein said bleaching activator comprises one or more water-insoluble bleaching activators selected from the group consisting of tetraacetyl ethylenediamine (TAED), n-nonanoyloxybenzenesulfonate (NOBS), and N-acetyl glucosamine, and combinations thereof.

11. The formulation according to claim 1 consisting of by weight:
    1-10% benzalkonium chloride;
    1-8% propylene glycol diacetate or glycerol diacetate;
    1-16% hydrogen peroxide;
    2-8% potassium bicarbonate;
    1-4% sorbent additive; and
    balance water.

12. The formulation according to claim 1, wherein said cationic surfactant comprises a quaternary ammonium salt comprising benzalkonium chloride.

13. The formulation according to claim 1, further comprising a cationic hydrotrope.

14. The formulation of claim 13, wherein the cationic hydrotrope is selected from the group consisting of tetrapentyl ammonium bromide, triacetyl methyl ammonium bromide, tetrabutyl ammonium bromide, and pentamethyltallow alkyltrimethylenediammonium dichloride.

15. The formulation according to claim 1 consisting essentially of said cationic surfactant, said reactive compound, said bleaching activator, said sorbent additive, said carbonate or bicarbonate salt, and water.

16. A formulation for use in neutralization of a toxant, said formulation comprising:
- at least one solubilizing compound selected from the group consisting of a cationic hydrotrope and a fatty alcohol comprising from 8 to 20 carbon atoms per molecule;
- a reactive compound comprising one or more compounds selected from the group consisting of hydrogen peroxide, urea hydrogen peroxide, hydroperoxycarbonate, peracetic acid, sodium perborate, sodium peroxypyrophosphate, sodium peroxysilicate, and sodium percarbonate;
- 1-4% by weight of a polyol sorbent additive selected from the group consisting of sorbitol, mannitol, hydrogenated starch hydrolysates, maltitol, zyiltol, lactitol monohydrate, anhydrous isomalt, erthritol, polydextrose and combinations thereof; and
- a bleaching activator selected from the group consisting of O-acetyl, N-acetyl and nitrile group bleaching activators;
- wherein said at least one solubilizing compound, said reactive compound, said sorbent additive, and said bleaching activator, when mixed with water and exposed to the toxant, neutralizes the toxant.

17. A formulation for use in neutralization of a toxant, said formulation comprising:
- a cationic surfactant;
- a reactive compound comprising one or more compounds selected from the group consisting of hydrogen peroxide, urea hydrogen peroxide, hydroperoxycarbonate, peracetic acid, sodium perborate, sodium peroxypyrophosphate, sodium peroxysilicate, and sodium percarbonate;
- a bleaching activator selected from the group consisting of O-acetyl, N-acetyl, and nitrile group bleaching activators; and
- 1-4% by weight a sorbent additive which is sorbitol;
- wherein said cationic surfactant, said reactive compound, said bleaching activator, said sorbent additive, and said carbonate or bicarbonate salt, when mixed with water and exposed to the toxant, neutralizes the toxant.

18. The formulation of claim 17, wherein the bleaching activator is propylene glycol diacetate or glycerol diacetate.

* * * * *